（12）United States Patent
Suga et al.

(10) Patent No.: US 10,195,578 B2
(45) Date of Patent: Feb. 5, 2019

(54) PEPTIDE LIBRARY PRODUCTION METHOD, PEPTIDE LIBRARY, AND SCREENING METHOD

(75) Inventors: Hiroaki Suga, Tokyo (JP); Jumpei Morimoto, Tokyo (JP)

(73) Assignee: The University of Tokyo, Tokyo (JP)

( * ) Notice: Subject to any disclaimer, the term of this patent is extended or adjusted under 35 U.S.C. 154(b) by 760 days.

(21) Appl. No.: 13/990,180

(22) PCT Filed: Dec. 5, 2011

(86) PCT No.: PCT/JP2011/078029
§ 371 (c)(1),
(2), (4) Date: Aug. 19, 2013

(87) PCT Pub. No.: WO2012/074130
PCT Pub. Date: Jun. 7, 2012

(65) Prior Publication Data
US 2014/0018257 A1  Jan. 16, 2014

(30) Foreign Application Priority Data
Dec. 3, 2010  (JP) .................. 2010-270507

(51) Int. Cl.
*C40B 50/06* (2006.01)
*B01J 19/00* (2006.01)
(Continued)

(52) U.S. Cl.
CPC ............. *B01J 19/0046* (2013.01); *C07K 7/08* (2013.01); *C07K 14/705* (2013.01);
(Continued)

(58) Field of Classification Search
None
See application file for complete search history.

(56) References Cited

U.S. PATENT DOCUMENTS

| 6,258,558 B1 | 7/2001 | Szostak et al. |
| 2003/0022230 A1 | 1/2003 | Yanagawa et al. |

FOREIGN PATENT DOCUMENTS

| EP | 2141175 A1 | 1/2010 |
| EP | 2615455 A1 | 7/2013 |

(Continued)

OTHER PUBLICATIONS

Matthews et al. (May 21, 1993) Science vol. 260 pp. 1113 to 1117.*
(Continued)

*Primary Examiner* — Christian C Boesen
(74) *Attorney, Agent, or Firm* — Suzannah K. Sundby, Esq.; Canady + Lortz LLP

(57) ABSTRACT

Object is to provide a method of constructing a library of peptides having, at a desired position in the random sequence of each peptide, an amino acid having a portion capable of binding to a target. The invention provides a method of producing a library of peptides having, at a designated position in the random sequence of each peptide, a special amino acid having a portion capable of binding to a target, including (i) preparing a library of mRNAs having, in the mRNA sequence coding for a random amino acid sequence, a base sequence having an altered codon encoding the special amino acid, (ii) preparing an aminoacyl tRNA with the special amino acid linked to a tRNA encoded by the altered codon, and (iii) translating the mRNAs by using a cell-free translation system containing the aminoacyl tRNA to obtain a library of peptides having, in the random sequence thereof, a predetermined special amino acid.

15 Claims, 2 Drawing Sheets

Specification includes a Sequence Listing.

(51) Int. Cl.

| C12N 15/10 | (2006.01) |
| --- | --- |
| C12N 15/67 | (2006.01) |
| C07K 7/08 | (2006.01) |
| C12Q 1/34 | (2006.01) |
| C07K 14/705 | (2006.01) |
| C40B 50/08 | (2006.01) |

(52) U.S. Cl.
CPC ......... *C12N 15/1062* (2013.01); *C12N 15/67* (2013.01); *C12Q 1/34* (2013.01); *B01J 2219/00725* (2013.01); *C40B 50/06* (2013.01); *C40B 50/08* (2013.01)

(56) References Cited

FOREIGN PATENT DOCUMENTS

| JP | 3683282 B2 | 8/2005 |
| --- | --- | --- |
| JP | 3683902 B2 | 8/2005 |
| JP | 3692542 B2 | 9/2005 |
| WO | 1998031700 A1 | 7/1998 |
| WO | 2000047775 A1 | 8/2000 |
| WO | 2003070740 A1 | 8/2003 |
| WO | 2010104115 A1 | 9/2010 |

OTHER PUBLICATIONS

Huhtiniemi, et al., "N, epsilon-modified lysine containing inhibitors for SIPT1 and SIRT2", Jun. 17, 2010, pp. 5616-5625, vol. 18, No. 15, Publisher: Bioorg Med Chem.

Kiviranta, et al., "N-epsilon-Thioacetyl-Lysine-Containing Tri-, Tetra-, and Pentapeptides as SIRT1 and SIRT2 Inhibitors", Apr. 9, 2009, pp. 2153-2156, vol. 52, No. 9, Publisher: Journal of Medicinal Chemistry.

Milne, et al., "The Sirtuin family: therapeutic targets to treat diseases of aging", Mar. 7, 2008, p. 1367-, vol. 12, No. 1, Publisher: Current Opinion in Chemical Biology.

Richard W. Roberts, et al., RNA-peptide fusions for the in vitro selection of peptides and proteins, The National Academy of Sciences, vol. 94, Nov. 1997, pp. 12297-12302.

Naoto Nemoto, et al., In vitro virus: Bonding of mRNA bearing puromycin at the 3'-terminal end to the C-terminal end of its encoded protein on the ribosome in vitro, Federation of European Biochemical Societies, 1997, pp. 405-408.

Clay Bracken, et al., Synthesis and Nuclear Magnetic Resonance Structure Determination of an a-Helical, Bicylic, Lactam-Bridged Hexapeptide, Journal of American Chemical Society, 1994, pp. 6431-6432.

David Y. Jackson, et al., General Approach to the Synthesis of Short a-Helical Peptides, Journal of American Chemical Society, 1991, pp. 9391-9392.

J. Christopher Phelan, et al., A General Method for Constraining Short Peptides to an a-Helical Conformation, Journal of American Chemical Society, vol. 119; No. 3, Jan. 22, 1997, pp. 455-460.

Helen E. Blackwell, et al., Highly Efficient Synthesis of Covalently Cross-Linked Peptide Helices by Ring-Closing Metathesis, Angewandte Chemie International Edition, vol. 37; No. 23, 1998, pp. 3281-3284.

Loren D. Walensky, et al., Activation of Apoptosis in Vivo by Hydrocarbon-Stapled BH3 Helix, American Association for the Advancement of Science, vol. 305, 2004, pp. 1466-1470.

Liu, et al., "LIU2009", "Evolution of Proteins with Genetically Encoded Chemical Warheads", Jul. 22, 2009, pp. 9616-9617, vol. 131, Publisher: Journal of the American Chemical Society, ACS Publications.

Kawakami, et al., "KAWAKAMI2009", "Diverse backbone-cyclized peptides via codon reprogramming", Dec. 25, 2009, pp. 888-890, vol. 5, No. 12, Publisher: Nature Chemical Biology.

Morimoto, et al., "MORIMOTO2012", "Discovery of Macrocyclic Peptides Armed with a Mechanism-Based Warhead: Isoform-Selective Inhibition of Human Deacetylase SIRT2", Feb. 28, 2012, pp. 3423-3427, vol. 15, No. 14, Publisher: Angewandte Chemie International Edition.

Higuchi, et al., "Programmed Synthesis of Natural Product-like Nonstandard Peptides Using the Translation System and Its Application" (2010) pp. 217-227, vol. 68, No. 3, Publisher: Journal of Synthetic Organic Chemistry, Published in: Japan (English translation of excerpt).

Hayashi, et al., "Ribosomal synthesis of nonstandard cyclic peptides and its application to drug discovery" (2010) pp. 505-514, vol. 82, No. 6, Publisher: The Journal of Japanese Biochemical Society. (English translation of excerpt).

Iida, et al., "Search of Special Peptide Drug by RaPID System", Sep. 24, 2010, pp. 71-78, Publisher: Chemistry Frontier 22 molecular tool for understanding life phenomenon—form imaging to vital function analysis (English translation of excerpt).

\* cited by examiner

PEPTIDE LIBRARY PRODUCTION METHOD, PEPTIDE LIBRARY, AND SCREENING METHOD

TECHNICAL FIELD

The present invention relates to a method of constructing a library composed of groups of peptidic molecules each containing, in a portion of the sequence thereof, a special amino acid; a library thus constructed, and a method of screening the library to select active peptides.

BACKGROUND ART

Low molecular compounds that have a structure similar to the substrate of an enzyme and bind to an active pocket of the enzyme have been used widely as an inhibitor of the enzyme. There is however a plurality of enzymes having a similar active pocket in the living body so that it is known that such low molecular compounds by themselves cannot easily serve as a specific inhibitor. On the other hand, peptidic molecules typified by antibodies have attracted attentions as next-generation pharmaceuticals because they can recognize the surface of a molecule over a wide range and specifically bind to a specific target.

For acquiring such peptidic molecules that bind to a specific target, a method of screening a random peptide library has been used widely. In particular, various in vitro display methods such as ribosome display method and mRNA display method using translation are excellent because a high diversity library can be constructed and screened in a tube in a short period of time. The term "in vitro display method" means a system facilitating concentration and amplification (selection) of active species by linking a phenotype and a genotype coding for the sequence thereof through a non-covalent bond or a covalent bond to display the phenotype on the genotype and using a replication system reconstructed in a test tube. The greatest characteristic of this system is that it is conducted without using a prokaryote or eukaryote as a medium so that a high-activity physiological substance can be isolated from a library having great diversity. As a typical comparison example, phage display using *Escherichia coli* as a replication medium enables selection from a library having diversity as high as $10^7$. In vitro display, on the other hand, enables searching from a library having diversity as high as $10^{12}$. Examples of the in vitro display include ribosome display, mRNA display, and RaPID display (unpublished international patent application PCT/JP2010/68549). As one example, mRNA display will next be described below.

The mRNA display method is a technology of binding a polypeptide to an mRNA which is a template thereof to match the amino acid sequence of the polypeptide to the nucleic acid sequence. By binding puromycin, which is an analogue of the end of an acylated tRNA, to the 3'-end of the mRNA via an appropriate linker and adding it to a translation reaction, puromycin penetrates in the site A of ribosome and forms a covalent bond with a growing peptide. As a result, the peptide molecule which is a translation product is linked to the mRNA via puromycin (Patent Documents 1 to 3, Non-patent Documents 1 and 2).

Thus, the in vitro display enables screening of a peptide library having diversity as high as $10^{12}$. Since such peptide library is constructed by making use of a vital function, however, only a peptide library composed only of proteinogenic amino acids has conventionally been constructed. It is expected that if it is possible to overcome the problem of this library composed only of proteinogenic amino acids; incorporate, in an amino acid structure, a low molecular inhibitor having insufficient inhibitory ability or specificity on its own; and construct and screen a library of peptides containing such special amino acid, inhibitors exhibiting high inhibitory ability and selectivity which cannot be attained by using a low molecular compound or a peptide alone can be obtained.

With recent development in technology called "genetic code expansion" or "reprogramming of genetic code", it actually becomes possible to prepare and screen a library of peptides having a special amino acid by using various display methods such as phage display.

In genetic code expansion, it becomes possible to synthesize proteins or peptides containing a special amino acid by making use of stop codons or artificial four-base codons which are not used for assigning an amino acid in a natural translation system and allocating these codons to the special amino acid. Since the number of stop codons or usable four-base codons is limited, the number of usable special amino acids simultaneously is however limited (substantially, three or less special amino acids).

There are three reports on construction and screening examples of a special peptide library by making use of this "genetic code expansion". The first one is on the construction of an N-methylphenylalanine-containing peptide library and screening of this library using mRNA display, which is made by R. Roberts, et al (Non-patent Document 3). According to this report, in spite of designing so that N-methyl-amino acid appears at a certain probability in a random peptide sequence, all the peptides obtained by actually screening with G protein as a target are composed of typical 20 amino acids and an N-methylphenylalanine-containing peptide is not obtained. The second one is on the construction of a peptide library incorporating sulfotyrosine therein and screening of this library using a phage, which is made by P. G. Schultz, et al. According to this report, they have succeeded in constructing a phage which has displayed scFv containing a random region designed so that sulfotyrosine appears at a certain probability and screening the library with gp120, the membrane protein of HIV virus, as a target and thereby actually acquiring scFv that contains sulfotyrosine and binds to gp120 (Non-patent Document 4). When the scFv thus obtained is expressed not in phage display but is expressed as a single substance, however, it becomes insoluble. In addition, it loses activity in the form of Fab so that an antibody having binding ability to a target has not yet been obtained in practice. The third report is on the construction of a library of peptides containing a special amino acid having a boron functional group that binds to saccharide and screening of this library by using a phage, which is also made by P. G. Schultz, et al (Non-patent Document 5). First, by constructing the above-described phage which has displayed scFv containing a random region designed so that a special amino acid appears at a certain probability and then screening the library using a substrate having a saccharide fixed thereon, they have succeeded in acquiring a sequence containing one or two of the special amino acids. There is however no finding that such peptide has specificity to a certain sugar or sugar chain. Also since the boron functional group originally has a property of forming a covalent bond with the hydroxyl group of sugar, the possibility of nonspecific binding between them cannot be denied. In short, a technology of acquiring scFv having a biologically significant peptide sequence that binds to a sugar chain or sugar protein has not yet been developed.

Any of the above-described technologies is limited to the construction of a library containing only one special amino acid and has not succeeded in acquiring a peptide containing desired physiological functions. They are therefore crude technologies from the standpoint of versatility and reliability of the technology.

Since the 2000s, "genetic code reprogramming" (reprogramming by initialization) in which a special amino acid is assigned to an vacant codon generated by removing a natural amino acid from the system has been developed, making it possible to use four or more special amino acids (Non-patent Documents 6 to 8). No examples have however been known yet in which a random peptide library containing a plurality of special amino acids is constructed by making use of genetic code reprogramming and a peptidic molecule that binds to a specific target is searched from the library.

PRIOR ART DOCUMENTS

Patent Documents

Patent Document 1: Japanese Patent No. 3683282 (International Publication WO98/16636)
Patent Document 2: Japanese Patent No. 3683902 (International Publication WO98/31700)
Patent Document 3: Japanese Patent No. 3692542

Non-patent Documents

Non-patent Document 1: Roberts et al., Proc. Natl. Acd. Sci. USA, 1997, 94, 12297-12302
Non-patent Document 2: Nemoto et al., FEBS Lett., 1997, 414, 405-408
Non-patent Document 3: SW. Millward, et al. ACS Chem. Biol. 2 625-634 (2007)
Non-patent Document 4: CC. Liu, et al. Proc. Natl. Acad. Sci. USA 105 17688-17693 (2008)
Non-patent Document 5: CC. Liu, et al. J. Am. Chem. Soc. 131 9616-9617 (2009)
Non-patent Document 6: Forester, A. C. et al.: Proc. Natl. Acad. Sci. USA, Vol. 100, p. 6353-6357 (2003)
Non-patent Document 7: Josephson, K., Hartman, M. C., Szostak, J. W.: J. Ame. Chem. Soc., Vol. 127, p. 11727-11735 (2005)
Non-patent Document 8: Murakami, H. et al.: Nat. Methods, Vol. 3, p. 357-359 (2006)

SUMMARY OF THE INVENTION

Problem to be Solved by the Invention

An object of the present invention is to provide a method of constructing a peptide library composed of peptides having, at a desired position of the random sequence thereof, an amino acid having a portion capable of binding to a target substance.

Means for Solving the Problem

The present inventors have found that by preparing an mRNA library having, in the base sequence thereof coding for a random amino acid sequence, an altered codon encoding an amino acid capable of binding to a target substance while preparing an aminoacyl tRNA by linking, to a tRNA corresponding to the altered codon, the amino acid capable of binding to a target substance, and translating the mRNA by using this aminoacyl tRNA, it is possible to obtain a library of peptides having, at a desired position in the random amino acid sequence thereof, the amino acid capable of binding to a target.

Described specifically, the present invention relates to the following:

[1] A method of producing, by translation, a peptide library containing peptides having, at a designated position in the random sequence thereof, a special amino acid having a portion capable of binding to a target substance, which includes:

(i) a step of preparing a library of mRNAs containing, in an mRNA sequence thereof coding for a random amino acid sequence, a base sequence having an altered codon encoding the special amino acid having a portion capable of binding to a desired target substance, (ii) a step of preparing an aminoacyl tRNA in which the special amino acid has been linked to a tRNA encoded by the altered codon, and (iii) a step of translating the mRNAs by using a cell-free translation system containing the aminoacyl tRNA to obtain a library composed of groups of peptides having, in the random sequence thereof, the predetermined special amino acid.

[2] The method described above in [1], wherein in the step (ii), the aminoacyl tRNA is prepared by transferring, to a tRNA, the special amino acid having a portion capable of binding to a desired target substance in the presence of an RNA catalyst having acyl tRNA synthetase-like activity.

[3] The method as described above in [1] or [2], wherein the altered codon encoding the special amino acid having a portion capable of binding to a desired target substance is an AUG codon and the mRNA random sequence is composed of repetition of an NNC or NNU (N represents any one base of A, U, G, and C) triplet.

[4] The method as described above in [3], wherein the mRNA random sequence further includes NNK (K represents U or G).

[5] The method as described above in any one of [1] to [4], further comprising a step of cyclizing each of the peptides.

[6] The method as described above in [5], wherein: in the step (i), second and third altered codons coding for two amino acids having functional groups 1 and 2 of any pair selected from below-described (A) to (C), respectively, are placed in the mRNA random sequence (with the proviso that when the amino acid having the functional group 2 is a proteinogenic amino acid, the third altered codon may be replaced by a codon encoding the proteinogenic amino acid), in the step (ii), an aminoacyl tRNA obtained by linking an amino acid having the functional group 1 to a tRNA encoded by the second altered codon and an aminoacyl tRNA obtained by linking an amino acid having the functional group 2 to a tRNA encoded by the third altered codon are prepared and the step (iii) is conducted using these tRNAs in addition, and after the step (iii), the method includes cyclization through a reaction between the functional groups.

TABLE 1

| | Functional group 1 | Functional group 2 |
|---|---|---|
| (A) | $-\overset{O}{\underset{\|}{C}}-\underset{H_2}{C}-X_1$ <br> (A-1) | HS— <br> (A-2) |

TABLE 1-continued

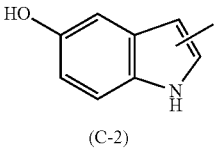

(wherein, $X_1$, represents Cl, Br, or I and Ar represents an aromatic ring which may have a substituent).

[7] The method as described above in any one of [1] to [6], wherein the special amino acid having a portion capable of binding to a desired target substance is a low molecular compound-containing special amino acid.

[8] The method as described above in any of [1] to [6], wherein the target substance is an enzyme and the portion capable of binding to a target substance is a low molecular group which is predicted to bind to an active site of the enzyme.

[9] The method as described above in any one of [1] to [8], wherein the step (i) further including a step of binding puromycin, directly or via a linker, to the 3'-end of each mRNA of the mRNA library thus obtained.

[10] A peptide library produced using the method as described above in any one of [1] to [9], wherein to each of the peptides is linked an mRNA coding for the peptide.

[11] A screening method of a peptide library obtained using the method as described above in any one of [1] to [9] or the peptide library as described above in [10] to select a peptide capable of binding to a target substance, including:

a step of bringing the peptide library into contact with the target substance, and a step of selecting a peptide that binds to the target substance.

A screening method of a peptide library obtained using the method as described above in [9] or the peptide library as described above in [10] to select a peptide capable of binding to a target substance, including:

a step of bringing the library into contact with the target substance, a step of selecting peptides that binds to the target substance and to which an mRNA has been linked, a step of synthesizing a DNA from the mRNA linked to the selected peptides through reverse transcription, a step of amplifying the DNA by using PCR, obtaining an mRNA library through transcription, and binding puromycin to each of the mRNAs, a step of translating the mRNA by using a cell-free translation system to obtain a library of peptides to each of which the mRNA has been linked, and a step of repeating, at least once, the steps from the step of bringing the library into contact with the target substance until the step of obtaining a peptide library.

Effect of the Invention

The present invention makes it possible to construct a library of peptides in which an amino acid having a portion capable of binding to a target has been placed at a desired position of a random amino acid sequence. Screening such a library enables to find peptides having such functions as enhanced affinity or specificity to the target compared with single use of the portion capable of binding to the target.

Such a library synthesized using a translation system is able to have extremely high diversity (for example, $10^{12}$ or more). Using it in combination with the in vitro display method makes it possible to efficiently conduct both concentration and identification of a peptide sequence having high affinity with the target.

In addition, according to the present invention, a library made of groups of peptides having, introduced therein, a special amino acid containing a low molecular compound capable of functioning as an enzyme inhibitor can be constructed. It is possible to acquire not a simple aptamer (binding active species) but an inhibitor showing high inhibitory ability and selectivity by screening this library.

BRIEF DESCRIPTION OF THE DRAWINGS

As shown in FIG. 2, the first schematically shown sequence is the NNK mRNA library sequence of SEQ ID NO: 10 and the sequences of its first, second, and third portions from left to right are as follows: SEQ ID NO: 71, SEQ ID NO: 72, and SEQ ID NO: 73. The second schematically shown sequence is the NNC mRNA library sequence of SEQ ID No: 12 and the sequences of its first, second, and third portions from left to right are as follows: SEQ ID NO: 74, SEQ ID NO: 75, and SEQ ID NO: 76. The peptide sequence at the C terminus of the schematically show sequence at the bottom of FIG. 2 is SEQ ID NO: 77.

MODE FOR CARRYING OUT THE INVENTION

Figure 1:
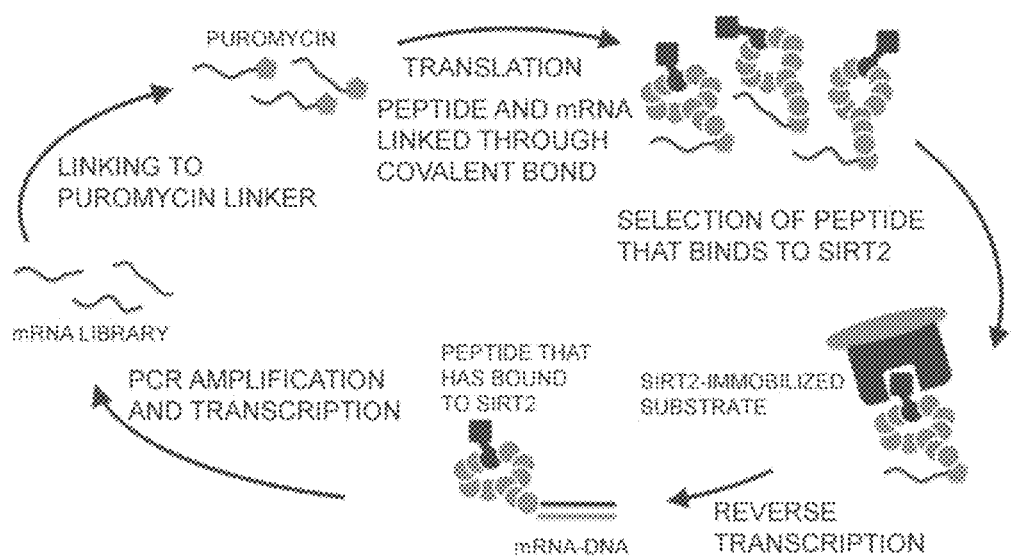
FIG. 1 shows selection of a special cyclic peptide library through mRNA display.

Prior to detailed description of the present invention, (A) genetic code reprogramming and (B) a preparation process of a cyclic peptide by making use of translation will be outlined as the background art.

(A) Genetic Code Reprogramming

In the translation in the living body, three base sequences (triplet) of mRNA encode for one amino acid as a codon and a peptide corresponding to the sequence is synthesized. The assignment of the codon to the amino acid is conducted in the following two stages. (i) To the end of tRNA is linked an amino acid corresponding thereto by aminoacyl tRNA synthetase (ARS). (ii) The tRNA anticodon matches with the mRNA codon corresponding thereto and the amino acid on the tRNA is polymerized along the information of the mRNA to synthesize a peptide.

Such a correspondent relationship between the codon and anticodon has been almost universally determined and any one of 20 amino acids is assigned for individual 64 codons. The following is a universal genetic code table.

TABLE 2

| Base of the first character ↓ | Base of the second character → U | | C | | A | | G | | Base of the third character ↑ |
|---|---|---|---|---|---|---|---|---|---|
| | Codon | Amino acid | Codon | Amino acid | Codon | Amino acid | Codon | Amino acid | |
| U | UUU | Phenylalanine | UCU | Serine | UAU | Tyrosine | UGU | Cysteine | U |
| | UUC | Phenylalanine | UCC | Serine | UAC | Tyrosine | UGC | Cysteine | C |
| | UUA | Leucine | UCA | Serine | UAA | Stop | UGA | Stop | A |
| | UUG | Leucine | UCG | Serine | UAG | Stop | UGG | Tryptophan | G |
| C | CUU | Leucine | CCU | Proline | CAU | Histidine | CGU | Arginine | U |
| | CUC | Leucine | CCC | Proline | CAC | Histidine | CGC | Arginine | C |
| | CUA | Leucine | CCA | Proline | CAA | Glutamine | CGA | Arginine | A |
| | CUG | Leucine | CCG | Proline | CAG | Glutamine | CGG | Arginine | G |
| A | AUU | Isoleucine | ACU | Threonine | AAU | Asparagine | AGU | Serine | U |
| | AUC | Isoleucine | ACC | Threonine | AAC | Asparagine | AGC | Serine | C |
| | AUA | Isoleucine | ACA | Threonine | AAA | Lysine | AGA | Arginine | A |
| | AUG | Methionine | ACG | Threonine | AAG | Lysine | AGG | Arginine | G |
| G | GUU | Valine | GCU | Alanine | GAU | Aspartic acid | GGU | Glycine | U |
| | GUC | Valine | GCC | Alanine | GAC | Aspartic acid | GGC | Glycine | C |
| | GUA | Valine | GCA | Alanine | GAA | Glutamic acid | GGA | Glycine | A |
| | GUG | Valine | GCG | Alanine | GAG | Glutamic acid | GGG | Glycine | G |

The above genetic codes can be reprogrammed by using a reconstituted translation system and flexizyme, that is, an artificial aminoacylating RNA catalyst.

The reconstituted translation system is a translation system obtained by isolating and purifying each of factors relating to translational synthesis of a protein or peptide, such as ribosome, translation factor, tRNAs, amino acids, and energy sources such as ATP and GEP and then mixing them. For example, technologies described in the following documents as a system using a ribosome of *Escherichia coli* are known: H. F. Kung, B. Redfield, B. V. Treadwell, B. Eskin, C. Spears and H. Weissbach (1977) "DNA-directed in vitro synthesis of beta-galactosidase. Studies with purified factors" The Journal of Biological Chemistry Vol. 252, No. 19, 6889-6894; M. C. Gonza, C. Cunningham and R. M. Green (1985) "Isolation and point of action of a factor from *Escherichia coli* required to reconstruct translation" Proceeding of National Academy of Sciences of the United States of America Vol. 82, 1648-1652; M. Y. Pavlov and M. Ehrenberg (1996) "Rate of translation of natural mRNAs in an optimized in vitro system" Archives of Biochemistry and Biophysics Vol. 328, No. 1, 9-16; Y. Shimizu, A. Inoue, Y. Tomari, T. Suzuki, T. Yokogawa, K. Nishikawa and T. Ueda (2001) "Cell-free translation reconstituted with purified components" Nature Biotechnology Vol. 19, No. 8, 751-755; H. Ohashi, Y. Shimizu, B. W. Ying, and T. Ueda (2007) "Efficient protein selection based on ribosome display system with purified components" Biochemical and Biophysical Research Communications Vol. 352, No. 1, 270-276.

Flexizyme is an artificial RNA catalyst (RNA catalyst having acyl tRNA synthetase-like activity) capable of linking (acylating) any amino acid or hydroxy acid to any tRNA. For example, those described in the following documents are known: H. Murakami, H. Saito, and H. Suga, (2003), "A Versatile tRNA Aminoacylation Catalyst Based on RNA" Chemistry & Biology, Vol. 10, 655-662; H. Murakami, D. Kourouklis, and H. Suga, (2003), "Using a solid-phase ribozyme aminoacylation system to reprogram the genetic code" Chemistry & Biology, Vol. 10, 1077-1084; H. Murakami, A. Ohta, H. Ashigai, H. Suga (2006) "The flexizyme system: a highly flexible tRNA aminoacylation tool for the synthesis of nonnatural peptides" Nature Methods 3, 357-359; N. Niwa, Y. Yamagishi, H. Murakami, H. Suga (2009) "A flexizyme that selectively charges amino acids activated by a water-friendly leaving group" Bioorganic & Medicinal Chemistry Letters 19, 3892-3894; and WO2007/066627, "Multi-purpose acylation catalyst and use thereof"). Flexizyme includes an original type flexizyme (Fx) and an altered type which is known as the name of dinitrobenzyl flexizyme (dFx), enhanced flexizyme (eFx), or amino flexizyme (aFx).

As a method capable of linking any amino acid to any tRNA, chemical aminoacylation method or the like can also be used.

For genetic code reprogramming, a translation system capable of freely removing component factors from the translation system, depending on the purpose, and then reconstituting the necessary components is used. For example, when a translation system from which a specific amino acid has been removed is reconstituted, the codon corresponding to the amino acid becomes an vacant codon. Next, by using flexizyme, chemical aminoacylation or aminoacylation with a mutant protein enzyme, a special amino acid is linked to a tRNA having an anticodon complementary to the vacant codon, followed by translation. As a result, the codon codes for the special amino acid and a peptide in which the special amino acid has been introduced instead of the removed amino acid is translated.

(B) Preparation Process of Cyclic Peptide by Making Use of Translation

It is considered that cyclized peptides have (i) improved protease resistance and (ii) increased rigidity and improved membrane permeability and affinity with a target protein. When peptides prepared by translation contain two or more cysteine residues, a cyclic structure can be formed via a disulfide bond. This bond is however easily reduced in vivo so that effects as described above cannot be expected so much. The present inventors therefore developed previously a method of cyclizing a linear translated peptide via a nonreducing bond and reported (Y. Goto, et al. ACS Chem. Biol. 3 120-129 (2008)). For example, a special peptide having, at the N-terminal thereof, a chloroacetyl group is synthesized using the above-mentioned genetic code reprogramming technology. By placing a cysteine residue in such peptide, due to spontaneous nucleophilic attack of a mercapto group against the chloroacetyl group after translation, the peptide is cyclized via a thioether bond. This means that a function of cyclic peptide is given by introducing a chloroacetyl group and a mercapto group, that is, a bond formable pair of functional groups into an amino acid sequence. Such a bond-formable pair of functional groups is not limited to a pair of a chloroacetyl group and a mercapto group. Details will be described later.

Peptide Library

Embodiments of the present invention will next be described.

The peptide library constructed according to the present invention is composed of groups of peptides having, at a desired position thereof, a special amino acid (which will hereinafter be called "Special Amino Acid") having a portion capable of binding to a target substance.

The library of peptides containing the Special Amino Acid is constructed by artificially assigning the Special Amino Acid to an existing codon by using in vitro translational synthesis using genetic code reprogramming. More specifically, by preparing a library of mRNAs having a codon coding for the Special Amino Acid and translating it by using an altered gene code table, it is possible to obtain a library of peptides having the Special Amino Acid introduced at a position designated by an altered codon.

Although no particular limitation is imposed on the length of the peptides constituting the peptide library, it is, for example, from 2 amino acids to 25 amino acids The term "codon" as used herein means both an altered codon and a universal codon to be used in natural translation. The altered codon is a codon which has lost its assignment to a proteinogenic amino acid and is assigned to a special amino acid by genetic code reprogramming. The special amino acid is encoded only by the altered codon.

The term "special amino acid" as used herein means any of amino acids different in structure from 20 proteinogenic amino acids to be used in a natural translation system and it may be either an artificially synthesized one or that occurring in nature. It embraces any of non-proteinogenic amino acids obtained by chemically changing or modifying a portion of the side chain structure of a proteinogenic amino acid, artificial amino acids, D-form amino acid, N-methyl-amino acid, N-acylamino acid, β-amino acid, and derivatives having a structure obtained by substituting an amino group or a carboxyl group on the amino acid skeleton.

In the present invention, special amino acids may be used as "the Special Amino Acid" or they may be used in the cyclization method which will be described later.

The Special Amino Acid has a portion capable of binding to a target substance. The portion capable of binding to a target substance can be predicted by various methods based on the structure of the target substance or an empirical rule. Although no particular limitation is imposed on the method of predicting the portion capable of binding to a target substance, it can be predicted, for example, by searching database of interaction between a receptor and a ligand; by using a variety of software capable of predicting the structure of a ligand from the structure of a receptor; or by predicting based on a molecule that binds to an analogous target substance. The portion that binds to the target substance may not be only a portion that binds to it but may be a portion increasing or decreasing the activity of the target substance.

The portion capable of binding to a target substance may be a portion that the special amino acid originally has or a portion introduced thereto artificially. In the former case, those selected from known special amino acids and having a portion capable of binding to a target substance can be used, while in the latter case, known special amino acids having, introduced therein, a portion capable of binding to a target substance can be used. Those skilled in the art can conduct the selection or introduction as needed by using a known method or a method equivalent thereto.

One example of the Special Amino Acid is a special amino acid containing a predetermined low molecular compound. Such a special amino acid will hereinafter be called "low molecular compound-containing special amino acid". Specific examples of the low molecular compound-containing special amino acid include special amino acids having a structure of a low molecular compound that binds to an enzyme active site of a target enzyme. The low molecular compound-containing special amino acid is placed at a position designated by an altered codon in a random amino acid sequence. In other words, surrounding sequences of the low molecular compound-containing special amino acid are randomized in the peptide library of the present invention.

By translationally introducing, into a peptide chain, an amino acid containing a low molecular compound that binds to a specific drug target site, for example, an enzyme catalyst site, there is a possibility of finding a special peptide having a function that cannot be exhibited only by the low molecular compound itself, for example, high affinity with a target or high specificity to the target.

In general, low molecular compounds that bind to a specific drug target site, for example, a catalyst activity site of an enzyme, have so far been found incidentally by studies employing random screening. Such initial low molecular compounds quite rarely had high affinity or specificity to a target and tremendous labor was spent for repeating synthesis and search on a trial and error basis, which is a more classical medicinal chemistry method. On the other hand, if as in the present invention, a known low molecular compound is incorporated in a peptide chain and a library having a randomized peptide sequence around the compound is constructed and searched, there is a possibility of enhancing the functionality of the low molecular compound. In such an approach, construction of a library inevitably depended on chemical synthesis and its diversity (about $10^6$) sufficient for searching is limited. The library of the present invention is synthesized using a translation system so that remarkably high diversity can be achieved.

In the present invention, the term "low molecular" is used in the broadest meaning of it. Although the molecular structure or molecular weight of the low molecular compound is not limited insofar as it is contained originally in the special amino acid or can be bound to the special amino acid, examples include molecules having from about 100 Da to 1000 Da.

The low molecular compound-containing special amino acid can be prepared as needed by those skilled in the art by using a known method or a method equivalent thereto. For example, according to the predicted structure of a low molecular compound capable of binding to a target substance, a special amino acid having the whole or a portion of the low molecular compound may be selected. Alternatively, the whole or portion of the predicted low molecular compound may be bound to the functional group of the special amino acid.

Structure that Binds to an Enzyme Active Site of Target Enzyme

The library of the present invention may be a library of peptides in which a low molecular compound-containing special amino acid capable of binding to an enzyme active site has been introduced in order to acquire not simply an aptamer but a peptide having inhibitory activity. In the present invention, the binding property of a lower molecular compound, a low molecular compound-containing special amino acid, or a peptide containing such a special amino acid to an enzyme active site may be called "enzyme active site directivity".

The structure permitting binding to an enzyme active site of a target enzyme may be designed theoretically based on the original structure of the substrate of the enzyme or, if a low molecular inhibitor that inhibits enzyme activity by binding to an active pocket is known, based on it. The low molecular compound is often a molecule not capable of acquiring sufficient physiologically active specificity to a target substance only by itself or a molecule which can be still expected to have improved activity.

For example, since in the active pocket of a sirtuin responsible for deacetylation of various intracellular proteins, $NAD^+$ and the ε-N-acetyllysine residue of a matrix protein bind to each other and deacetylation reaction proceeds, an analogue of $NAD^+$ or ε-N-acetyllysine residue can be used as an inhibitor. The most representative inhibitor contains nicotinamide, which is a portion of an $NAD^+$ structure, and ε-N-trifluoroacetyllysine or ε-N-thioacetyllysine. Any inhibitor however has its limit in specificity between isoforms or in inhibitory ability. It is therefore expected that an inhibitor having improved specificity or improved inhibitory activity can be obtained by constructing a library of peptides having, introduced therein, a special amino acid having the whole or a portion of the structure of such an inhibitor and optimizing the sequence by screening. In Examples which will be described later, a peptide showing a certain level of isoform selectivity and having markedly high inhibitory ability was obtained in practice by constructing a library of peptides containing ε-N-trifluoroacetyllysine and screening it with SIRT2, that is, a human sirtuin as a target. A similar effect can be expected by constructing a library of peptides having, introduced therein, a special amino acid having an ε-N-thioacetyllysine or nicotinamide structure and screening the library.

[Chemical formula 1]

1. ε-N-trifluoroacetyllysine

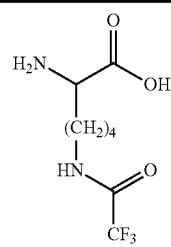

ε-N-thioacetyllysine

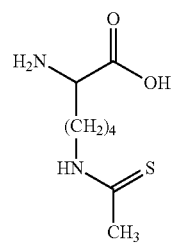

With regard to other enzymes, a number of methods for predicting, based on their enzyme reaction mechanism, a low molecular compound capable of enhancing or inhibiting enzyme activity are known.

Production Method of Peptide Library

Next, a description will be made on a production method of a peptide (which may hereinafter be called "Special Peptide") having, at a desired position in the random amino acid sequence thereof, a Special Amino Acid.

The peptide library of the present invention is produced by a method including:

(i) a step of preparing a library of mRNAs having, in the mRNA sequence thereof coding for a random amino acid sequence, a base sequence having an altered codon encoding an amino acid having a portion that binds to a desired target substance;

(ii) a step of preparing an aminoacyl tRNA in which the special amino acid has been linked to a tRNA encoded by the altered codon, and (iii) a step of translating the mRNA by using a cell-free translation system containing the tRNA to which the special amino acid has been linked and thereby obtaining a library of groups of peptides having, in the random sequence thereof, a predetermined special amino acid.

The step (i) and the step (ii) may be conducted in any order. Alternatively, they may be conducted in parallel.

Cell-Free (In Vitro) Translation System

First, a cell-free translation system will be described.

The term "translation system" means a system for peptide translational synthesis and it is generally a concept including both a method and a kit (substance). In the present invention, as the cell-free translation system to be used for the preparation of a special peptide library, either a known reconstituted translation system or a system constructed by subdividing the known reconstituted translation system and reducing impurities as much as possible may be used. Specific constituents of the translation system as a kit (substance) usable in the present invention will next be described, while comparing it with the conventional system.

Specific examples of the constituents of the translation system include ribosome, translation initiation factor (IF) group, elongation factor (EF) group, release factor (RF) group, ribosome recycling factor (RRF), a minimum set of natural amino acid, tRNA, and a specific ARS protein enzyme which will become necessary in the synthesis of an intended peptide, and an energy source for translation reaction.

As the ribosome, that isolated from *Escherichia coli* and then purified is preferably used.

As the proteins, used are translation initiation factors (for example, IF1, IF2, and IF3), translation elongation factors (for example, EF-Tu, EF-Ts, and EF-G), translation release factors (for example, RF1, RF2, RF3, and RRF), and enzymes for regeneration of an energy source (for example, creatine kinase, myokinase, pyrophosphatase, and nucleotide-diphosphatase kinase). Among them, translation release factors and enzymes for regeneration of an energy source may be added as desired. Although T7 RNA polymerase may be added for the transcription from a template DNA, RNA polymerase is not necessary if mRNA transcribed in advance is added to the translation system.

In addition, similar to the conventional system, an appropriate buffer solution, an NTP as an energy source of a translation reaction, Creatine phosphate, and factors necessary for ribosome activation, RNA stabilization, and protein stabilization can be used as needed. In the typical translation reaction, N-formylmethionine is defined as initiation codon AUG by an initiator tRNA so that a formyl donor such as 10-formyl-5,6,7,8-tetrahydroforlic acid (Baggott et al., 1995) is essential. In the present invention, when a translation reaction is started with the special amino acid, a formyl donor is optional. For the same reason, methionyl-tRNA formyltransferase (MTF) is also not essential.

In the translation system to be used in the present invention, for natural proteinogenic amino acids, natural tRNA and ARS corresponding to natural proteinogenic amino acids can be used as in the conventional system. Natural tRNA is, for example, a mixture obtained by collecting *Escherichia coli*, disrupting it, and purifying the tRNA fraction. It can also be commercially available. The specific A, U, C, and G in the natural tRNA have been chemically modified with an enzyme. Alternatively, a tRNA having a natural sequence transcribed in a test tube can also be used. On the other hand, for the special amino acid, not natural tRNA but artificial tRNA, which is a tRNA transcript, is preferably used as an orthogonal tRNA. The artificial tRNA can be prepared by in vitro transcription reaction using an appropriate PRNA polymerase while using DNA as a template. No chemical modification can be found from such an artificial tRNA.

In order to introduce the special amino acid into the peptide which is a translation product, orthogonal tRNA acylated with the special amino acid in advance is added to the translation system. In a preferred mode, the tRNA acylated with the special amino acid is prepared by binding the special amino acid to the 3'-end of an orthogonal tRNA isolated, by using flexizyme, under conditions free of the other tRNA or ARS. In principle, it is also possible to use a tRNA to which the special amino acid has been linked chemically or enzymatically. The aminoacylation reaction with the special amino acid will be described later in detail.

Template Nucleic Acid Coding for Special Peptide

In the present invention, a library of peptides having a random amino acid sequence is synthesized by carrying out translational synthesis from a template nucleic acid (mRNA or DNA corresponding thereto) having a random sequence in a region coding for a peptide in the cell-free translation system. Construction of a peptide library therefore includes preparation of a library composed of nucleic acids coding for respective peptides and translation of it.

In the present invention, the sequence of an RNA or DNA coding for the Special Peptide is designed so that it codes for a linear or cyclic special peptide in which a predetermined special amino acid has been introduced at a designated position in a random sequence. Examples of the predetermined special amino acid include low molecular compound-containing special amino acids.

In order to cause a proteinogenic amino acid to appear at random in the random sequence, the codon sequence of an mRNA serving as the template thereof is designed. It may be designed so that all the 20 proteinogenic amino acids appear or some of the proteinogenic amino acids appear. At any position of such a random mRNA codon sequence, an altered codon encoding the Special Amino Acid is placed. Only one or two or more of the Special Amino Acids may be introduced into the peptide chain.

It is the common practice to employ NNK (in which N represents any base selected from G, A, C, and U and K represents U or G) as the codon sequence of the template mRNA in order to construct a library having peptide sequences at random. When the Special Amino Acid is assigned to, for example, AUG (as described above, AUG is usable as both an initiation codon and elongation codon), one of elongation codons and a peptide library is constructed using a library of NNK, AUG appears at random as one codon represented by NNK so that a plurality of the Special Amino Acids are incorporated in the peptide library. This means that when repeated triplets of the NNK sequence are used as a random sequence, there is a possibility of one or more special amino acids which are encoded by AUG being placed at an unintended position.

When AUG is used as the codon encoding the Special Amino Acid, using repeated triplets made of an NNU or NNC sequence as a random sequence makes it possible to avoid appearance of AUG in the random sequence and to cause the Special Amino Acid to appear selectively at one or more desired positions of the peptide chain.

Using a library of bases having a random sequence of NNU or NNC prevents appearance of five amino acids (Met, Trp, Gln, Lys, and Glu). NNK may be used in addition to NNU and NNC if the merit of causing them to appear exceeds the demerit of placing the Special Amino Acid at a position other than the desired position.

It is also possible to use a codon corresponding to an amino acid, which does not appear when NNU or NNC is used, for introducing a special amino acid (for example, a special amino acid having a functional group to be used for cyclization), other than the Special Amino Acid, at a designated position. For example, four codons, UGG, CAG, AAG, and GAG in addition to AUG can be used for allocating them to the special amino acid for cyclization.

The mRNA including NNU, NNC, and NNK can be obtained by synthesizing DNA including NNT, NNC, and NNK by using a various DNA synthesizer, followed by transcription.

In the present invention, DNA or RNA molecules corresponding to a base sequence serving as a translation template are added to a cell-free translation system comprised of components optimized according to the intended use. Similar to a protein expression system making use of living cells, the nucleic acid sequence may include a region coding for an intended amino acid sequence and in addition, a base sequence advantageous for translation, depending on a translation system to be employed. For example, in a system using ribosome derived from *Escherichia coli*, the efficiency of a translation reaction increases when the sequence contains, upstream of the initiation codon, Shine-Dalgarno (SD) sequence, epsilon sequence, or the like.

An initiation codon is placed at the N terminal of a region coding for a peptide. The initiation codon is typically a triplet sequence AUG. Since the initiation codon can be reprogrammed when an anticodon sequence is not limited in the initiator tRNA synthesized through the in vitro transcription reaction, another base sequence, as well as the AUG codon, can also be used as the initiation codon.

As described later in detail, the Special Peptide may be a cyclized one.

In order to obtain a cyclized peptide, the RNA or DNA sequence may be designed by making use of an intermolecular reaction of a linear special peptide obtained by translational synthesis.

For example, a region of a base sequence coding for a peptide contains base sequences corresponding to the following (a) to (d) in the order of mention along the direction from 5' to 3' of the mRNA sequence:

(a) a first altered codon encoding a special amino acid having a functional group 1, (b) a random sequence composed of a plurality of repeated triplets, (c) a second altered codon placed at any position in the random sequence and encoding the Special Amino Acid, and (d) a codon encoding an amino acid having a functional group 2.

The functional group 1 and the functional group 2 are, as will be described later, a pair of functional groups capable of undergoing a bond formation reaction.

When an amino acid having the functional group 2 is a proteinogenic amino acid, a codon encoding the amino acid is a corresponding universal codon and when an amino acid having the functional group 2 is a special amino acid, a codon encoding the amino acid is a third altered codon.

In one mode of the present invention, the special amino acid having the functional group 1 for cyclization is an amino acid at the N-terminal of a peptide and is introduced by an initiator tRNA through a translation initiation reaction. On the other hand, the low molecular compound-containing special amino acid is introduced by an elongator tRNA through a peptide chain elongation reaction. The initiator tRNA introduces an amino acid, which has been matched with and linked to the AUG codon at the translation initiation position, to the N terminal of the peptide and an AUG codon at the other positions is matched with an elongator tRNA having a CAU codon. Two amino acids are therefore assigned to the AUG codon via two tRNAs, respectively. To avoid confusion, the AUG codon matched with an initiator tRNA will hereinafter be called "initiation AUG codon" and the AUG codon matched with an elongator tRNA will hereinafter be called "elongation AUG codon" or called simply "AUG codon".

When "first mode" which will be described later is employed for cyclization of a peptide, an amino acid having the functional group 2 is a proteinogenic amino acid encoded by a universal codon.

When "second mode" which will be described later is employed for cyclization of a peptide, an amino acid having the functional group 2 is a special amino acid and is encoded by a third altered codon which is an elongation codon. The third altered codon is a sequence other than AUG.

When a "third mode" or a "fourth mode" which will be described later is employed for cyclization of a peptide, both a special amino acid having a functional group 1 for cyclization and an amino acid having a functional group 2 are introduced into a peptide chain through an elongation reaction. In the "third mode", the first altered codon is a sequence other than the initiator AUG and the proteinogenic amino acid having the functional group 2 is encoded by a universal codon. In the "fourth mode", both the first altered codon and the third altered codon are elongator codons and a sequence other than initiation AUG is assigned to it.

In the peptide library according to the present invention, peptides constituting a library may have a constitution with nucleic acid sequences coding for these peptides by using the in vitro display technology in combination. By using this constitution, a library having a phenotype (amino acid sequences of peptides) displayed on a genotype (nucleic acid sequences) is constructed. In other words, a peptide aptamer is selected from a display library displaying genetic information as peptides, which are translation products of it. This means that random peptide molecules in the library are each attached with a tag which can be amplified and read by a molecular biological method.

In the in vitro display, peptides synthesized using a cell-free translation system (also called "in vitro translation system") are displayed while being assigned to genetic information. As this method, ribosome display, mRNA display, DNA display, and the like are known. Rapid display (refer to International Publication No. 2011/049157) can also be used. Each display method has a mechanism of linking the genetic information recorded in mRNA or DNA to a peptide encoded by the genetic information and thereby assigning them as a [genetic information]—[translation product] complex. In the ribosome display, mRNA-ribosome-peptide forms a triple complex. In the mRNA display and RAPID display, an mRNA-peptide complex is formed. In DNA display, a DNA-peptide complex is formed. In the present invention, any in vitro display library can be used. The in vitro selection, which is a screening method using the in vitro display library, will be described later.

When used in combination with the in vitro display, the RNA or DNA sequence coding for the Special Peptide may have, on the 3' end side of the sequence, a sequence for linking a nucleic acid molecule to a peptide which is a translation product thereof. For example, in an mRNA display method using a puromycin linker, an mRNA-peptide complex library is formed by adding, to a translation system, an mRNA library linked preliminarily with a puromycin linker. The linker is inserted typically between the 3' end side of the mRNA and puromycin in order to efficiently incorporate puromycin in the A site of a ribosome. Puromycin functions as a substrate (aminoacyl tRNA analogue) of a peptide transfer reaction on the ribosome and it links between mRNA and the peptide by binding to the C-terminal of the elongation peptide. The mRNA display method is a technology of integrating genotype and phenotype with each other by linking an mRNA and a peptide via an appropriate linker in an in vitro translation system. Insofar as such an object is achieved, puromycin may be replaced by a linker containing another substance having a similar function, which is within a range of the recognition of those skilled in the art.

As another method, it is also possible to use a method of forming an mRNA-peptide complex library by hybridization of a linker and an mRNA in an in vitro translation system instead of using an mRNA linked preliminary with a linker. For example, an mRNA-peptide complex library is formed by using a phenylalanine linker (3'-phenylalanine-ACCA-PEG-[a base sequence complementary to the 3'-end region of an mRNA library]-5') prepared by making use of flexizyme and a strand complementary to the mRNA library in combination ("RAPID display method" described in PCT/JP2010/685459). In this case, a region of the mRNA coding for a peptide contains, downstream (3' end region) thereof, a base sequence for hybridization with the linker.

In Example which will be described specifically later, an initiation AUG codon is placed at the N terminal of a peptide and a codon UGC coding for cysteine (Cys) as an amino acid having the functional group 2 is placed at the C terminal of the peptide. Immediately after it, a codon coding for GlySerGlySerGlySer (SEQ ID NO: 70) serving as a linker follows. The initiation AUG codon and UGC have therebetween a random sequence and an AUG codon encoding the Special Amino Acid is placed at the center of the random sequence.

Preparation of tRNA Having Special Amino Acid Linked Thereto

In the present invention, an aminoacyl tRNA necessary for assignment of the special amino acid is prepared by aminoacylating an isolated tRNA in vitro. The term "aminoacylating an isolated tRNA in vitro" means that a desired amino acid is bound to the 3'-end of the tRNA under conditions free of another tRNA or ARS. Such an aminoacylation method is preferably applicable to any amino acid. As such an aminoacylation method, a chemical aminoacylation method (Heckler T. G., Chang L. H., Zama Y., Naka T., Chorghade M. S., Hecht S. M.: T4 RNA ligase mediated preparation of novel "chemically misacylated" $tRNA^{Phe}_s$. Biochemistry 1984, 23:1468-1473) and a method using an aminoacyl tRNA synthesis ribozyme (ARS ribozyme) developed by the present inventors are known. Although not applicable to any amino acid, a method of using an enzyme obtained by artificially modifying a natural ARS is also usable.

In the present invention, a method of aminoacylating a tRNA in vitro is most preferably a synthesis method making use of an ARS ribozyme. As the ARS ribozyme, flexizyme developed by the present inventors is preferably used.

Flexizyme is an RNA catalyst (ARS ribozyme) having a function of acylating an amino acid substrate having a desired structure into a desired tRNA. Different from natural ARS protein enzymes, flexizyme has no specificity to each amino acid or each tRNA and is capable of conducting aminoacylation with any amino acid other than the amino acid to be linked. More specifically, it does not contain an α-substituent at the recognition site of an amino acid so that not only L amino acid but also hydroxy acid (having a hydroxyl group at the α position), α-N-methylamino acid, α-N-acylamino acid, or D-amino acid can be used as a substrate. In addition, an amino acid modified after translation such as ε-N-acetyllysine or ε-N-methyllysine can also be used as a substrate. Details on it are described in, in addition to the above-mentioned document on flexizyme, the following documents: Y. Goto, H. Suga (2009) "Translation initiation with initiator tRNA charged with exotic peptides" Journal of the American Chemical Society, Vol. 131, No. 14, 5040-5041, WO2008/059823 "Translation and synthesis of polypeptide having normative structure at n-terminus and application thereof", Goto et al., ACS Chem. Biol., 2008, 3, 120-129, T. J. Kang, et al., Chem. Biol., 2008, 15, 1166-1174 "Expression of histone H3 tails with combinatorial lysine modifications under the reprogrammed genetic code for the investigation on epigenetic markers", and WO2008/117833 "Process for synthesizing cyclic peptide compound".

In the present invention, the special amino acid is introduced into a peptide sequence by adding, to a cell-free translation system, orthogonal tRNA acylated with the special amino acid by using flexizyme.

The orthogonal tRNA is a tRNA capable of efficiently causing an amino acid, which has been designated after paired with the codon of mRNA, to express in a peptide synthesis reaction on a ribosome, though it is not aminoacylated in a translation system because it is not recognized by naturally occurring ARS (for example, ARS protein enzyme derived from *Escherichia coli*) inherent in the translation system. As the orthogonal tRNA, for example, a natural suppressor tRNA derived from a different species or an artificially constructed tRNA is used. In the present invention, as described above, an orthogonal tRNA which is an artificial transcript is preferably used for the introduction of the special amino acid.

Flexizyme has catalytic ability with an activated amino acid ester as a substrate. It recognizes a carbonyl group which is a reaction point of an amino acid, an aromatic ring in the amino acid side chain or in the leaving group, and the 5'-RCC-3' sequence portion (R represents A or G) present at the 3' end of a tRNA and thereby acrylates them into adenosine at the 3'-end. Flexizyme has no specificity to the anticodon portion of the tRNA. This means that even if the anticodon portion of the tRNA is changed to any sequence, it has no influence on the efficiency of aminoacylation. Since any special amino acid can be linked to a tRNA having any anticodon sequence by using flexizyme, the any special amino acid can be assigned to any codon. This therefore makes it possible to produce a library having any special amino acid introduced therein.

The following is a known flexizyme structure (RNA sequence).

Original flexizyme Fx (SEQ ID NO: 1)

[5'-GGAUCGAAAGAUUUCCGCAGGCCCGAAAGGGUAUUGGCGUUAG GU-3', 45 nt]

Dinitrobenzyl flexizyme dFx (SEQ ID NO: 2)

[5'-GGAUCGAAAGAUUUCCGCAUCCCCGAAAGGGUACAUGGCGUUA GGU-3', 46 nt]

Enhanced flexizyme eFx (SEQ ID NO: 3)

[5'-GGAUCGAAAGAUUUCCGCGGCCCCGAAAGGGGAUUAGCGUUAG GU-3', 45 nt]

Aminoflexizyme aFx (SEQ ID NO: 4)

[5'-GGAUCGAAAGAUUUCCGCACCCCCGAAAGGGGUAAGUGGCGUU AGGU-3', 47 nt]

Since different from natural ARS protein enzyme, flexizyme catalyzes only a procedure of binding an amino acid substrate to tRNA while skipping a procedure of forming a high energy intermediate (aminoacyl AMP), which is the first stage of an aminoacylation reaction, it is necessary to use, as an amino acid substrate, an amino acid weakly activated in advance. This means that instead of skipping adenylation of an amino acid, an amino acid derivative having a weakly activated ester bond at a carbonyl group at which acylation proceeds is used. Activation of an acyl group is usually achieved by forming an ester bond with a leaving group having an electrophilic property, but an ester having a too strong electrophilic leaving group not only undergoes hydrolysis in water but also causes random acylation of an RNA. It is therefore necessary to use a weakly activated amino acid substrate to prevent such a side reaction in a catalyst free state. Such weak activation can be achieved by using AMP, a cyanomethyl ester, a thioester, or a benzyl ester or the like having an electrophilic functional group such as nitro group or fluorine. Preferred examples of the amino acid substrate include, but not limited to, aminoacyl-cyanomethyl ester (CME: cyanomethyl ester), aminoacyl-dinitrobenzyl ester (DNB: 3,5-dinitrobenzyl ester), and aminoacyl-4-chlorobenzyl thioester (CBT: p-chloro-benzyl thioester).

The amino acid substrate should have, in the amino acid side chain or leaving group thereof, an aromatic ring so as to be recognized by flexizyme. As the substrate of flexizyme, such an amino acid substrate having an appropriate leaving group may hereinafter be called "activated amino acid ester". For example, in the case of ε-N-acetyllysine, ε-N-acetyllysine-bound tRNA lysine can be prepared by using ε-N-acetyllysine-CBT as a substrate and mixing eFx with tRNA. Since eFx recognizes the 4-chlorobenzyl group in the leaving group but does not recognize the amino acid side chain, an analogue such as ε-N-trifluoroacetyllysine-CBT or ε-N-thioacetyllysine-CBT can be used similarly as the substrate of eFx.

[Chemical formula 2]

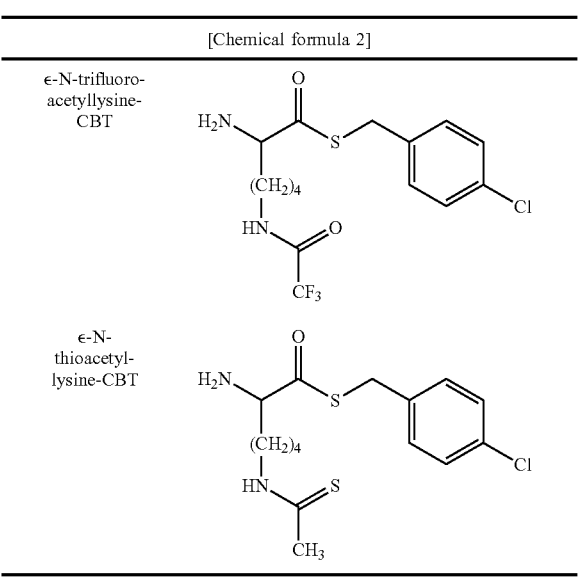

ε-N-trifluoro-acetyllysine-CBT

ε-N-thioacetyl-lysine-CBT

The acylation reaction by using flexizyme may be conducted either in a solution or in a column using an ARS ribozyme immobilized on a substrate. For example, when the scale of the translation reaction is as small as 100 μl or less, it is recommended to conduct acylation of tRNA in a solution by using flexizyme; dissolve pellets, which have been obtained by precipitating the reaction solution in ethanol, in a proper buffer (for example, 1 mM potassium acetate, pH 5 or the like); and add the resulting solution to a translation system. As the reaction conditions, preferable conditions may be selected as needed. The following is one example of the conditions of a small-scale reaction. It is recommended to react a 0.1M reaction buffer of pH 7.5 containing from 0.5 to 20 μM a tRNA, from 0.5 to 20 μM flexizyme, from 2 to 10 mM an amino acid substrate, and 0.6M $MgCl_2$, each in terms of a final concentration, at 0° C. for from 1 to 24 hours.

When the scale of the translation reaction exceeds 100 μl, it is convenient to use flexizyme immobilized on a substrate in consideration of reuse of the flexizyme. Examples of the substrate include, but not particularly limited to, resins, agarose, sepharose, and magnetic beads. When the reaction is conducted while immobilizing flexizyme on a substrate, it may be conducted, for example, in the following manner: Murakami, H., Bonzagni, N. J. and Suga, H. (2002), "Aminoacyl-tRNA synthesis by a resin-immobilized ribozyme", J. Am. Chem. Soc. 124(24): 6834-6835. Isolation of the aminoacylated tRNA as a reaction product can be conducted using various methods. One example is to elute it from a column with a buffer containing about 10 mM EDTA. The resin on which an ARS ribozyme has been immobilized can be used in repetition a dozen times, for example, by equilibrating it with a reaction buffer.

In Example which will be described later, an example of linking an acetyllysine analogue to $tRNA^{Asn-E2}$ and introducing it in an amino acid sequence will be described. The $tRNA^{Asn-E2}_{NNN}$ is an artificial tRNA prepared by modifying $tRNA^{Asn}$, which is an elongation reaction tRNA derived from Escherichia coli, and it can be used by changing the anticodon sequence (NNN, in which N represents any base) in various ways, but when a second altered codon encoding an acetyllysine analogue is AUG, the sequence of the anticodon becomes CAU. Since this artificial tRNA has orthogonality to natural ARS, a natural amino acid is not linked thereto in the translation system, but it is accepted without a problem in the peptide-chain elongation reaction on a ribosome. This means that the aminoacyl tRNA obtained by linking a special amino acid to the artificial tRNA binds to an elongation factor (EF-Tu), is transferred to the site A of the ribosome and is used in a peptide chain elongation procedure. The $tRNA^{Asn-E2}$ is one example of an elongator tRNA for acylating a special amino acid and its usability has been confirmed in the practical cell-free translation system used in Example. The elongator tRNA which can be used in the present invention is not limited to it. Those skilled in the art can understand that the tRNA usable for introducing a special amino acid in the peptide chain elongation reaction in the present invention can be selected as needed depending on the component of the cell-free translation system to be employed.

In the present invention, even when the amino acid having a functional group for cyclization is a special amino acid, such a special amino acid is bound to an orthogonal tRNA having any anticodon by using flexizyme. In one mode of the present invention, an amino acid having the functional group 1 is placed as the initiation amino acid residue. In this case, by linking an amino acid having a functional group for cyclization reaction to an initiator tRNA, the functional group for cyclization reaction is introduced at the N terminal of the peptide. For example, in Example which will be described later, $N^\alpha$-chloroacetyl-L(D)-tyrosine, that is, an L-form or D-form tyrosine having a chloroacetyl group was linked to $tRNA^{fMet}$, that is, an initiator tRNA, and it was introduced at the N terminal of a peptide. The chloroacetyl group introduced into the peptide causes a spontaneous $S_N2$ reaction with the mercapto group of the cysteine residue inside the peptide and the peptide was cyclized via a thioether bond (Goto et al., ACS Chem. Biol., 2008, 3, 120-129). In this example, tyrosine was used as a mother nucleus, but a peptide library can also be produced without a problem from an L-form or D-form of the other 19 proteinogenic amino acids.

Initiator tRNA and Elongator tRNA

It is important that in a natural translation reaction, an initiator tRNA is used only in the initiation of translation but not in an elongation reaction and on the contrary, an elongator tRNA is not used in the initiation reaction. This difference between the initiator tRNA and the elongator tRNA is also applied to the present invention.

In the present application, an artificial tRNA is preferably used for acylation of the special amino acid. A non-restrictive example of the artificial tRNA which is an elongator tRNA is $tRNA^{Asn-E2}$. The base sequence of this tRNA is based on natural $tRNA^{Asn}$ (5'-UCCUCUG$^{s4}$UA-GUUCAGDCGGDAGAACGGCGGACUQUU$^{t6}$AAYCC-GUAU$^{m7}$GUCACUGGTY CGAGUCCAGUCAGAG-GAGCCA-3' (SEQ ID NO: 7)) of Escherichia coli ($^{s4}$U: 4-thiouridine, D: dihydrouridine, Q: queuosine, $^{t6}$A: 6-threo-nylcarbamoyladenine, Y: pseudouridine, $^{m7}$G: 7-methyl-guanosine, T: ribothymidine). The present inventors removed a modified base from this natural tRNA and introduced mutation thereinto and thereby prepared $tRNA^{Asn-E2}$, that is, an elongator tRNA not influenced by aminoacylation with 20 aminoacylation enzymes of Escherichia coli through in vitro transcription. The NNN site corresponds to an anticodon and it is changed so as to correspond to a codon.

($tRNA^{Asn-E2}$: 5'-GGCUCUGUAGUUCAGUCGGUA-GAACGGCGGACU NNNAAUCCGUAUGUCACUGGUUCGAG UCCAGU-CAGAGCCGCCA-3' (SEQ ID NO: 5) [modification removed at eight places in total: $^{s4}$U8U, D16U, D20U, $^{r6}$A37A, Y39U, $^{m7}$G46G, T54U, and Y55U. The thirty-fourth Q is an anticodon so that it is changed so as to correspond to a codon] [mutated at four sites in total: U1G, C2G, G71C, and G72C].

A non-restrictive example of the artificial tRNA which is an initiator tRNA is tRNA$^{fMet}$. The base sequence of this tRNA is based on natural tRNA$^{fMet}$ (5'-CGCGGGG$^{s4}$UGGAGCAGCCUGGDAGCUCGUCGGG-CmUCAUAACCCGAAGAUCGUCGGTY CAAAUCCG-GCCCCCGCAACCA-3' (SEQ ID NO: 8)) of *Escherichia coli* (Cm: 2'-O-methylcytidine). The present inventors removed a modified base from this natural tRNA and changed the first C of the 5' end to G and thereby prepared tRNA$^{FMat}$, that is, a tRNA for initiation reaction through in vitro transcription. The CAU site corresponds to an anticodon and corresponds to an initiation AUG codon. (tRNA$^{fMet}$ used in the present application: 5'-GGCGGGGUGGAGCA-GCCUGGUAGCUCGUCGGGCU CAUAACCCGAAGAUCGUCGGUUCAA AUCCGC-CCCCGCAACCA-3', (SEQ ID NO: 6) [modification removed at six places in total: $^{s4}$U8U, D20U, Cm32C, T54U, Y55U][mutated at one site: C1G]). It is important for the initiator tRNA that the first base at the 5' end (C in the natural tRNA$^{fMet}$ and G in the tRNA$^{fMet}$ of the present application) does not form a complementary strand with the seventy second base (A in the natural tRNA$^{fMet}$ and the tRNA$^{fMet}$ of the present application). This non-complementary strand transfers a formyl group to Met-tRNA$^{Fmet}$, recognized by methionylformyl transferase (MTF) (with the proviso that when a special amino acid for initiation is used, it does not have any meaning) or it suppresses EF-Tu binding.

Cyclization of Peptide

In one mode of the present invention, the peptide library may be made of cyclic peptides. A method of cyclizing a peptide is not particular limited, but it may be cyclized, for example, by making use of an intramolecular specific reaction of a noncyclic peptide obtained by translational synthesis. The cyclization of a peptide is conducted through the following steps (i) and (ii):

(i) a step of synthesizing, by translational synthesis, a noncyclic peptide compound having, in the molecule thereof, a pair of functional groups, that is, a functional group 1 and a functional group 2, capable of undergoing a bond formation reaction; and (ii) a step of cyclizing the noncyclic peptide compound through the bond formation reaction between the functional group 1 and the functional group 2.

The term "a pair of functional groups capable of undergoing a bond formation reaction" means a pair of functional groups capable of undergoing a bond formation reaction therebetween, that is, between the functional group 1 and the functional group 2 and as a result of the reaction, converting the noncyclic peptide compound into a cyclic peptide compound. No particular limitation is imposed on such a pair of functional groups insofar as it is a pair capable of undergoing a bond formation reaction. In addition, no particular limitation is imposed on the reaction manner between the functional groups and various reaction manners such as substitution reaction, addition reaction, condensation reaction, and cyclization addition reaction can be employed. Moreover, no particular limitation is imposed on the form (single bond, double bond, triple bond, or the like) and number of the bond to be formed by the reaction.

Examples of the pair of the functional groups include a pair of —CH$_2$-L (L represents a leaving group such as —Cl, —Br, or —OSO$_2$CH$_3$) and a nucleophilic functional group (—OH, —NH$_2$, —SH, or the like). One example of the bond formation reaction between the functional group 1 and the functional group 2 is formation of a cyclic structure through a disulfide bond between two cysteine residues. The disulfide bond is easily reduced in vivo so that in order to obtain a stable cyclic structure, the bond between the functional group 1 and the functional group 2 is preferably a non-reducing bond.

The present inventors previously developed and reported a method of cyclizing a translated linear peptide through formation of a non-reducing bond (Goto et al., ACS Chem. Biol., 2008, 3, 120-129, WO2008/117833 "Process for synthesizing cyclic peptide compound"). A similar method can be employed in the present application. The term "noncyclic peptide compound" means a noncyclic compound embraced in the Special Peptide and has the same meaning as a linear peptide.

The following is a preferred example of the pair of the functional group 1 and the functional group 2 usable in the present invention.

[Chemical formula 3]

| | Functional group 1 | Functional group 2 |
|---|---|---|
| (A) | 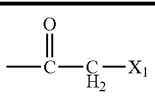 (A-1) | HS— (A-2) |
| (B) | —C≡C—H (B-1) | N$_3$— (B-2) |
| (C) | —Ar—CH$_2$NH$_2$ (C-1) | 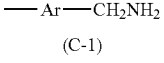 (C-2) |

(wherein, X$_1$ represents Cl, Br, or I and Ar is an aromatic ring which may have a substituent).

Although no particular limitation is imposed on the substituent of Ar, examples of it include a hydroxyl group, halogen atoms, alkyl groups having from 1 to 6 carbon atoms, alkoxy groups having from 1 to 6 carbon atoms, a phenyl group, a phenoxy group, a cyano group, and a nitro group.

The pair (A) can provide a structure of the formula (A-3) through a substitution reaction between the functional groups. The pairs (B) and (C) can provide structures (B-3) and (C-3) through a cyclization reaction between the functional groups, respectively.

[Chemical formula 4]

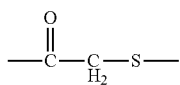 (A-3)

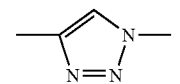 (B-3)

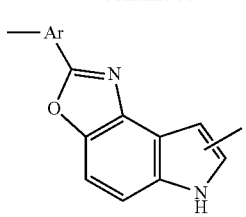
(C-3)

Since a ring is formed through bond formation between paired functional groups present in a noncyclic peptide compound, it is necessary that the paired functional groups are present on different constituent units with a constituent (typically, amino acid) of the noncyclic peptide compound as one unit. For convenience of description, such a constituent and a constituent unit will hereinafter be called "amino acid compound" and "amino acid compound unit", respectively. In short, the noncyclic peptide compound is a compound having paired functional groups on different amino acid units, respectively. The noncyclic peptide compound has preferably at least one amino acid compound unit between one amino acid compound unit having one of the functional groups and an amino acid compound unit having the other functional group.

In the present invention, a noncyclic peptide compound having such a pair of functional groups is synthesized through translational synthesis in a cell-free translation system. When the amino acid having these functional groups for cyclization is not a proteinogenic amino acid but the special amino acid, it may be introduced into a peptide chain by making use of genetic code reprogramming technology.

In a first mode, translational synthesis of a noncyclic peptide compound is conducted through a method including a step of providing (a) an initiator tRNA aminoacylated with an amino acid having the functional group 1, (b) a cell-free translation system containing at least an amino acid having the functional group 2 and a tRNA to be aminoacylated with the amino acid, and (c) an mRNA having, at a desired position thereof, a codon corresponding to an anticodon of the initiator tRNA and an anticodon of the initiator tRNA and a codon corresponding to an anticodon of the tRNA to be aminoacylated with the amino acid having the functional group 2; and adding the aminoacylated initiator tRNA (a) and the mRNA (c) to the cell-free translation system (b) to synthesize a corresponding noncyclic peptide compound.

The noncyclic peptide compound obtained by the method according to the first mode, translation starts with the special amino acid having the functional group 1 and the functional group 2 is present on a proteinogenic amino acid residue introduced in the peptide chain elongation reaction.

In the first mode, when the amino acid having the functional group 1 is encoded by an AUG codon and introduced at the peptide N-terminal, a cell-free translation system not containing methionine is preferably used. The system is however not limited to it.

The functional group 1 may be present as a substituent on the carbon atom such as α-carbon or β-carbon of the amino acid or may be present on a substituent on such carbon atom. In addition, the functional group 1 may be present as a substituent on the nitrogen atom of the amino group or may be present on a substituent on such nitrogen atom of the amino group. The functional group 1 and the functional group 2 are required to be able to undergo a bond formation reaction. As will be described later, since the functional group 2 is basically a nucleophilic functional group (—SH, —COOH, —OH, or the like) contained in cysteine, tyrosine, or the like, the functional group 1 is preferably a functional group having an appropriate leaving group, for example, —CH$_2$-L (L represents a leaving group such as —Cl, —Br, —I, or —OSO$_2$CH$_3$).

The special amino acid having the functional group 1 is preferably an amino acid compound having, on the amino group nitrogen atom thereof, the group of (A-1). Specific examples of the amino acid compound include the compounds of the following formula (1):

[Chemical formula 5]

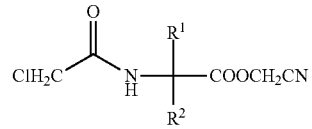
(1)

In the formula (1), R$^1$ and R$^2$ each represent a hydrogen atom or any substituent linked to the α-carbon atom via carbon. More specifically, R$^1$ and R$^2$ are preferably any of substituents on the α-carbon of 20 proteinogenic amino acids and R$^1$ and R$^2$ are preferably any combination of substituents on the α-carbon of proteinogenic amino acids. Specific examples of the compound of the formula (1) include compounds of the following formula (I-1):

[Chemical formula 6]

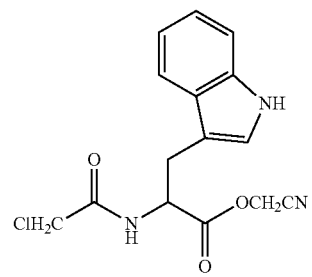
(1-1)

The amino acid having the functional group 2 is, for example, cysteine, aspartic acid, glutamine, or tyrosine. This means that the functional group 2 is —OH, —SH, —C(=O)NH$_2$, —COOH, or the like. The amino acid having the functional group 2 is preferably cysteine. The amino acid having the functional group 2 is introduced through a peptide chain elongation reaction by using a reconstituted translation system containing at least the amino acid and a tRNA corresponding thereto.

When the functional group 2 is a proteinogenic amino acid, the proteinogenic amino acid can be introduced into a peptide chain by not using an altered codon but using a codon encoding an aminoacyl tRNA to which the proteinogenic amino acid has been linked.

In another method according to a second mode for the synthesis of a cyclic peptide compound, both the amino acid having the functional group 1 and the amino acid having the functional group 2 are special amino acids. The functional group 1 and the functional group 2 may be present as a substituent on the amino group nitrogen atom or as a substituent on the carbon atom such as α-carbon or β-carbon.

When they are present on the nitrogen atom, they may be introduced onto the nitrogen atom of the amino acid amino group as an acyl substituent, for example, as represented by the following formulas (20) to (24):

[Chemical formula 7]

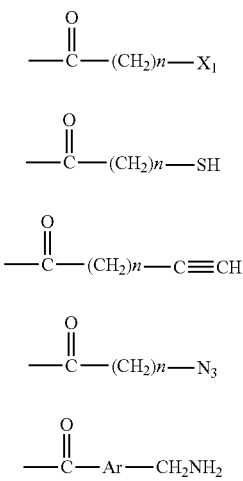

(20)
(21)
(22)
(23)
(24)

(wherein, n stands for an integer of 1 or greater, for example, an integer from 1 to 10, and $X_1$ has the same meaning as described above) or a portion of the acyl substituent.

When they are present on the carbon atom such as α-carbon or β-carbon, they can be introduced as a group, for example, as represented by the following formulas (25) to (30):

[Chemical formula 8]

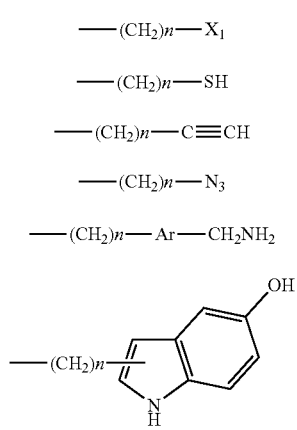

(25)
(26)
(27)
(28)
(29)
(30)

(wherein, n stands for an integer of 1 or greater, for example, an integer from 1 to 10 and $X_1$ has the same meaning as described above).

Specific examples of the amino acid compound having the functional group 1 include compounds represented by the following formula (2) and specific examples of the amino acid compound having the functional group 2 include compounds represented by the following formula (3).

[Chemical formula 9]

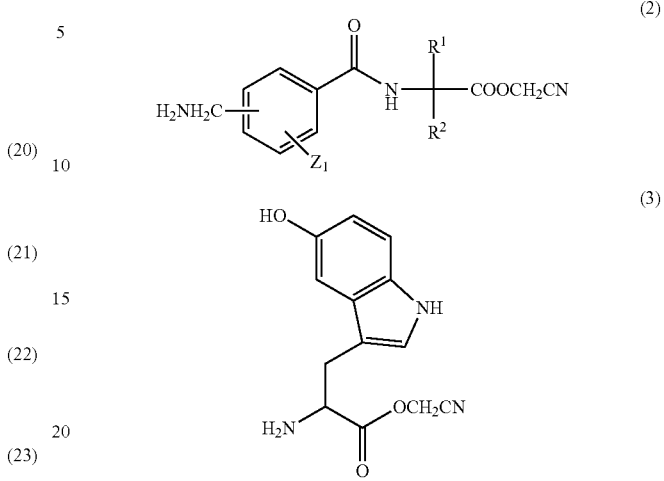

(2)
(3)

In the formula (2), $R^1$ and $R^2$ have the same meaning as described above and $Z_1$ represents any substituent. Examples of $Z_1$ include a hydroxyl group, halogen atoms, alkyl groups having from 1 to 6 carbon atoms, alkoxy groups having from 1 to 6 carbon atoms, a phenyl group, a phenoxy group, a cyano group, and a nitro group. Specific examples of the compound of the formula (2) include compounds of the following formula (31):

[Chemical formula 10]

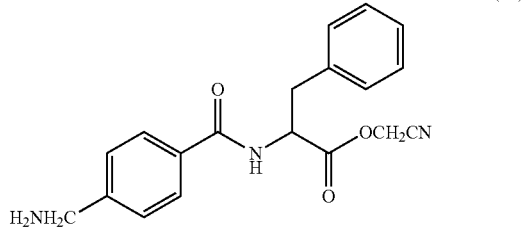

(31)

In a further method according to a third mode for the synthesis of a cyclic peptide compound, the both the functional group 1 and the functional group 2 are present on an amino acid residue to be introduced in the peptide chain elongation reaction. The amino acid having the functional group 1 is the special amino acid and is introduced in a peptide chain elongation reaction by using a gene reprogramming technology. Similar to the first mode, the amino acid having the functional group 2 is a proteinogenic amino acid. Since the functional group 2 is basically a nucleophilic functional group (—SH, —COOH, —OH, or the like) contained in cysteine, tyrosine, or the like, the functional group 1 is preferably a functional group having an appropriate leaving group, for example, —CH$_2$-L (L represents a leaving group such as —Cl, —Br, —I, or —OSO$_2$CH$_3$).

Specific examples of the amino acid compound having the functional group 1 include compounds of the following formula (4):

[Chemical formula 11]

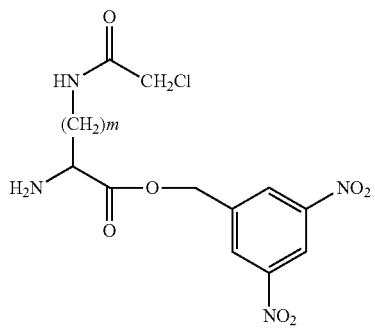

(4)

In the formula (4), m stands for an integer from 1 to 10. Specific examples of the compound (4) include a compound wherein m stands for 2 and this compound can be prepared, for example, from 2,4-diaminobutyric acid. The amino acid compound having the functional group 2 is preferably cysteine.

In a still further method according to a fourth mode for the synthesis of a cyclic peptide compound, both the functional group 1 and the functional group 2 are present on an amino acid residue to be introduced in a peptide chain elongation reaction. The both the amino acid having the functional group 1 and the amino acid having the functional group 2 are the special amino acids and introduced into a peptide chain by using a gene code reprogramming technology.

The functional group 1 and the functional group 2 can be present as a substituent on the amino group nitrogen atom or a substituent on the carbon atom such as α-carbon or β-carbon. The functional group 1 and the functional group 2 are preferably present as a substituent on the carbon atom such as α-carbon or β-carbon. Examples of the functional group 1 and the functional group 2 include those exemplified above in the second mode.

Specific examples of the amino acid having the functional group 1 include compounds of the formula (5) or formula (7).

[Chemical formula 12]

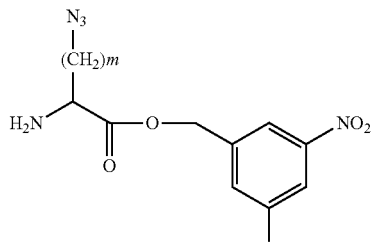

(5)

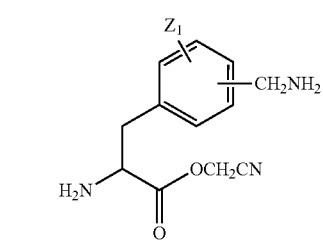

(7)

In these formulas, $Z_1$ and m each have the same meaning as described above. Specific examples of the compound of the formula (7) include compounds of the following formula (32):

[Chemical formula 13]

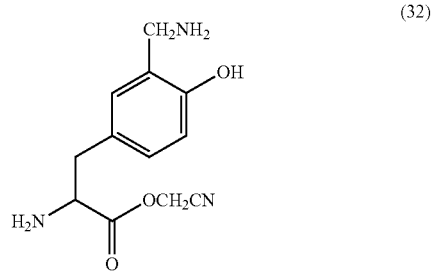

(32)

Specific examples of the amino acid having the functional group 2 include compounds of the following formula (6) or the formula (8).

[Chemical formula 14]

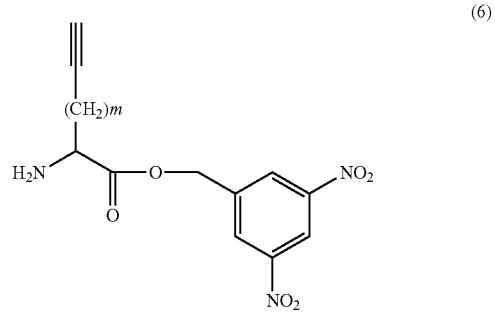

(6)

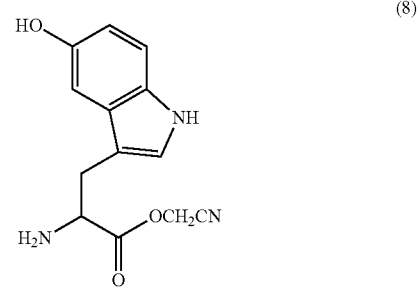

(8)

In the formula (6), m has the same meaning as described above.

Additional examples of the amino acid compound having the functional group 1 include compounds (for example, the compound of the above formula (4)) having the functional group (A-1) and those of the amino acid compound having the functional group 2 include —SH-containing special amino acid such as homocysteine or mercapto-norvaline.

A cyclic peptide compound can be obtained by cyclizing the noncyclic peptide compound synthesized as described above. The conditions of the bond formation reaction between the functional group 1 and the functional group 2 are determined, depending on the kinds of the paired functional groups.

Cyclization of the noncyclic peptide compound can be conducted by isolating the noncyclic peptide compound and then exposing it to appropriate reaction conditions. Cyclization can also be conducted by not isolating the noncyclic peptide compound but controlling the conditions of the cell-free translation system to appropriate ones. Depending on the kind of the paired functional groups, cyclization may occur under the conditions of the cell-free translation system for synthesizing the noncyclic peptide compound and in this case, a cyclic peptide compound can be obtained without particularly controlling the reaction conditions.

Cyclization of the noncyclic peptide compound is conducted, for example, under the following reaction conditions. When the paired functional groups are —$CH_2$-L (L represents a leaving group such as —Cl or —Br) and a nucleophilic functional group —SH, cyclization can be conducted, for example, by isolating the noncyclic peptide compound and then heating (for example, from 40 to 100° C.) it in an appropriate solvent or by keeping the cell-free translation system, for example, at from 35 to 40° C. for several hours (for example, at 37° C. for three hours) without isolating the noncyclic peptide compound.

When the pair of the functional groups is the above-mentioned pair (A), cyclization can be achieved, for example, by isolating the noncyclic peptide compound and then heating (for example, from 40 to 100° C.) it in an appropriate solvent or by keeping the cell-free translation system, for example, at from 35 to 40° C. for several hours (for example, at 37° C. for three hours) without isolating the noncyclic peptide compound. Since the reactivity between the functional groups (A-1) and (A-2) is relatively high, when the pair of the functional groups is the above-mentioned pair (A), the reaction of the functional groups proceeds in the cell-free translation system for the synthesis of the noncyclic peptide compound and a cyclic peptide compound may be isolated from the cell-free translation system.

When the pair of functional groups is the above-mentioned pair (B), the structure (B-3) can be formed by treating the non-cyclic peptide compound, which has been isolated from the cell-free translation system, with a monovalent copper salt (prepared while reducing copper sulfate (II) with an ascorbate in the system) in an appropriate solvent and thereby conducting cyclization (Huisgen cyclization) of the resulting compound.

When the pair of functional groups is the above-mentioned pair (C), the structure (C-3) can be formed by isolating the noncyclic peptide compound and then treating it with potassium ferricyanide ($K_3[Fe(CN)_6]$) in an appropriate solvent.

In Example which will be described later, a cyclic peptide obtained by translational synthesis of a peptide sequence having at both ends thereof a chloroacetyl group and cysteine, respectively, is described as an example that can be cyclized under the conditions of the cell-free translation system. In this case, a peptide having, as the functional group 1, a chloroacetyl group can be synthesized by using genetic code reprogramming technology. When a cysteine residue is left in the peptide (for example, at the C-terminal thereof), nucleophilic attack of the mercapto group against the chloroacetyl group occurs spontaneously after the translation and the peptide is cyclized through a thioether bond. When a chloroacetyl group is introduced at the N-terminal of a peptide, an initiator tRNA acylated with a chloroacetyl-containing amino acid is added to a methionine-free translation system to synthesize a corresponding peptide. Alternatively, the chloroacetyl group may be placed at a site other than the N-terminal and in this case, an elongator tRNA acylated with a chloroacetyl-containing amino acid and a methionine-containing translation system are used.

When even numbers of cysteine residues have appeared in the random sequence in addition to the C-terminal, there is a possibility of formation of a peptide having a plurality of cyclic structures formed with a thioether bond between the chloroacetyl group and any one of cysteines and a disulfide bond between the remaining cysteines.

Screening Method

The peptide library thus produced is useful for screening for selecting the Special Peptide capable of binding to a target substance.

In one mode, the screening method includes a step of bringing a peptide library into contact with a target substance and a step of selecting a peptide that binds to the target substance.

The target substance is not particularly limited herein and it is, for example, a low molecular compound, a high molecular compound, a nucleic acid, a peptide, a protein, or the like.

The target substance, for example, fixed on a solid-phase substrate can be brought into contact with the library of the present invention. The "solid-phase substrate" to be used herein is not particularly limited insofar as it is a substrate onto which a target substance can be fixed and examples include microtiter plates made of, glass, a metal, a resin, or the like, a substrate, beads, nitrocellulose membrane, nylon membrane, and PVDF membrane. The target substance can be fixed to such a solid-phase substrate in a known manner.

The target substance and the library are brought into contact with each other in a buffer selected as needed to react them while controlling the pH, temperature, time, or the like.

The screening method according to one mode of the present invention further includes a step of selecting the Special Peptide bound to the target substance. Prior to binding the peptide to the target substance, the peptide is detectably labeled by a known method. After the step of bringing them into contact, the surface of the solid phase is washed with a buffer to detect the peptide which has bound to the target substance. Examples of the detectable label include enzymes such as peroxidase and alkaliphosphatase, radioactive substances such as $^{125}I$, $^{131}I$, $^{35}S$, and $^{3}H$, fluorescent substances such as fluoresceine isothiocyanate, rhodamine, dansyl chloride, phycoerythrin, tetramethyl rhodamine isothiocyanate, and infrared fluorescent materials, light-emitting substances such as luciferase, luciferin, and aequorin, and nanoparticles such as gold colloid and quantum dot. When the label is an enzyme, the peptide may be detected by adding a substrate of the enzyme to develop a color. The peptide may also be detected by binding biotin thereto and then binding avidin or streptoavidin labeled with an enzyme or the like to the biotin-binding peptide.

It is possible not only to detect or analyze the presence/absence or degree of binding but also to analyze the enhanced or inhibited activity of the target substance and thereby identify the Special Peptide having such enhancing or inhibitory activity. Such a method makes it possible to identify the Special Peptide having physiological activity and useful as a pharmaceutical.

In Vitro Selection

In the present invention, the special peptide library constructed in the cell-free translation system can be completely adapted to the in vitro display technology including mRNA display so that it is possible to create peptide molecules that bind to a target from the high-diversity special peptide library having $10^{12}$ or more peptides.

The in vitro display technology is utilized as a tool of evolutionary molecular engineering. In this evolutionary molecular engineering, with a view to creating proteins or peptides having a desired function or property, genes having this possibility are prepared on a large scale and a clone having a desired phenotype is selected from them. Basically, first, a DNA group (DNA library) is produced. Then, an RNA group (RNA library) is produced as an in vitro transcript, followed by production of a peptide group (peptide library) as an in vitro translation product. From this peptide library, peptides having a desired function or property are selected by using some screening system. For example, when a peptide molecule that binds to a certain protein is desired, a peptide group is poured in a column containing a target protein as a solid phase and a mixture of the peptide molecule bound to the column can be collected. At this time, each peptide molecule is attached with a nucleic acid molecule, which is a template of the peptide molecule, as if a tag. In mRNA display library, each peptide molecule is attached with mRNA. Then the group of peptide-mRNA complexes thus collected is returned to DNA by using a reverse transcriptase and then amplified by using PCR to obtain a biased library containing many clones having a desired phenotype. Then, a similar selection test is conducted again. It is also possible to conduct a reverse transcription reaction before selection in order to change the nucleic acid portion to a double strand (DNA/RNA hybrid) and thereby avoid possible collection of an RNA aptamer. By repeating this operation, a clone having a desired phenotype is concentrated in the group with the passage of the generation.

In order to identify a peptide aptamer, a gene of the peptide aptamer that binds to a target substance can be cloned by repeating a step of mixing an in vitro display library and the target substance; selecting an assigning molecule (active species) displaying the peptide that has bound to the target substance; and preparing a nucleic acid library by using PCR from the nucleic acid portion of the assigning molecule thus selected.

As the target substance, usually any compound such as protein, peptide, nucleic acid, carbohydrate, or lipid may be used.

In order to select the active species, it is necessary to bring a [genetic information]-[peptide] complex into contact with the target substance and isolate and collect a complex that displays the peptide bound to the target substance from many other complexes not bound to the target substance. Many technologies are known as such a collection method.

For example, it is convenient to give the target substance some modification which can be collected by binding to a solid phase. In Example which will be described later, for example, a polyhistidine tag linked to the target substance can be collected by making use of specific binding of the polyhistidine tag to a substrate having Ni-NTA supported thereon. Examples of such specific binding include, in addition to a combination of biotin-binding protein (avidin, streptoavidin, or the like)/biotin, a combination of maltose-binding protein/maltose, polyhistidine peptide/metal ion (nickel, cobalt, etc.), glutathione-S-transferase/glutathione, and antibody/antigen (epitope) combinations, but specific binding is not limited to them.

The present invention includes creating a special peptide that binds to a target substance by repeating in vitro selection having the following steps: bringing a peptide library to a target substance, selecting an active species displaying the peptide that has bound to the target substance, amplifying the nucleic acid sequence of the thus-selected active species, and selecting the active species from the library of peptides synthesized again in a cell-free translation system with the amplified nucleic acid sequence as a template. Specific examples of the target substance include enzymes. In particular, using a library including enzyme active site-directed peptides enables to acquire peptides that not only bind to a target enzyme but have enzyme inhibitory activity.

According to one mode of the screening method of the present invention using the in vitro selection includes: a step of bringing a library into contact with a target substance, a step of selecting a peptide to which an mRNA that binds to the target substance has been linked, a step of synthesizing a DNA from the mRNA linked to the selected peptide through reverse transcription, a step of amplifying the DNA by using PCR, obtaining an mRNA library through transcription, and binding puromycin to each of the mRNAs, a step of translating the mRNA by using a cell-free translation system to obtain a peptide library to which the mRNA has been linked, and a step of repeating, at least once, the steps from the step of bringing the library into contact with the target substance to the step of obtaining a peptide library. As these steps are repeated, peptides having high affinity with the target substance are concentrated.

Creation of a special peptide compound that binds to a target substance includes collecting peptides that have bound to the target substance, analyzing the nucleic acid sequence which have bound to the peptides, determining a peptide sequence from the nucleic acid sequence, selecting appropriate special peptides based on the resulting peptide sequence, and obtaining an amino acid sequence and a nucleic acid sequence of the special peptides that bind to the target substance. Moreover, based on the sequence information thus obtained, special peptides can be synthesized, purified, and isolated by using a desired method. By evaluating binding of the resulting peptides to the target substance and confirming their inhibitory activity, special peptides with high activity can be obtained. When the target substance is an enzyme, the enzyme inhibitory activity of the resulting peptides is evaluated and peptides having enzyme inhibitory activity can be screened.

When the screening method of the present invention is used for selecting from the peptide library peptides that bind to the enzyme active site of a target enzyme, the method may include the following steps:

(i) a step of preparing a library including enzyme active site-directed peptides, (ii) a step of bringing the peptide library to the target substance; and (iii) a step of selecting peptide molecules that bind to the target substance.

This method may further include the following step (secondary screening stage) to select from the peptide library peptides having enzyme inhibitory activity:

(a) a primary screening stage for selecting peptides that bind to a target enzyme, and (b) a secondary screening stage for evaluating the enzyme inhibitory activity of the peptides selected in the primary screening stage and determining that these peptides are peptides having enzyme inhibitory activity; the primary screening stage further including:

(i) a step of preparing a library including enzyme active site-directed peptides, (ii) a step of bringing the peptide library into contact with a target enzyme molecule; and (iii) a step of selecting a peptide molecule that binds to the target enzyme molecule.

Moreover, a method of synthesizing a selected peptide by a proper process and thereby preparing a peptide having enzyme inhibitory activity is also within the scope of the present invention. The peptide synthesized in such a manner and having enzyme inhibitory activity is also within the scope of the present invention.

Construction Method of Peptide Library with SIRT2 as Target and Method of Acquiring Inhibitory Peptide Therefrom A method of constructing a peptide library while using as a target SIRT2 which will be described later in Example and a method of acquiring an inhibitory peptide will hereinafter be described (FIG. 1). The mode described herein is exemplary only and the present invention is not limited to or by the mode.

Target Protein SIRT2

Acetylation of a lysine residue, which is one of modifications following protein translation, is controlled dynamically by the action of various acetylation enzymes and deacetylation enzymes. Sirtuins are one of such deacetylation enzymes and it is known that there are seven human sirtuins from SIRT1 to SIRT7. Although the in vivo action of sirtuins has not yet been understood completely, relation of SIRT2 with cancers or neurodegenerative diseases has been elucidated. Surtuin inhibitors are attracting attentions [1),2),3)].

As one of sirtuin inhibitors, there is a peptidic inhibitor obtained by taking out, from a substrate protein of a sirtuin, only a sequence in the vicinity of a sequence to be deacetylated and converting the acetyllysine site into an acetyllysine analogue. Since ε-N-trifluoroacetyllysine ($^{Tfa}K$), one of such analogues, binds strongly to the active pocket of a sirtuin and a detrifluoroacetylation rate of it by surtuin is by far lower than a deacetylation rate of it, a peptide containing it serves as a powerful inhibitor of surtuin [4)]. In the development of such peptidic inhibitors, a sequence in a substrate protein of surtuin has been used continuously as a peptide sequence surrounding an acetyllysine analogue.

The present inventors have therefore tried to acquire a peptide sequence showing a stronger inhibitory effect by constructing a random peptide library having $^{Tfa}K$ and screening it.

Construction of mRNA Library

First, in order to construct a peptide library through translation, an mRNA library serving as a template is prepared. Although the length of the sequence of a portion of the mRNA to be translated is not limited, five kinds of lengths within a range of from 16 to 20 codons are prepared this time. These sequences each have, at the N terminal thereof, an initiation AUG codon (first altered codon) and have, on the C terminal side, a codon UGC coding for Cys, followed by a codon coding for GlySerGlySerGlySer which will be a linker. The initiation AUG codon and the codon UGC have therebetween a random codon sequence of NNK, NNC, or NNU (N represents any one base of A, U, G, and C and K represents either one base of U and G). In this random sequence, an AUG codon (second altered codon) is placed as only one specific codon for special amino acid introduction.

Construction of Peptide Library

The above-mentioned mRNA library is translated under an altered genetic code table. More specifically, a translation system is constructed while removing methionine from typical 20 amino acids and instead of it, (i) tRNA$^{fMet}_{CAU}$ to which α-N-chloroacetylated amino acid has been linked and (ii) tRNA$^{AsnE2}_{CAU}$ to which $^{Tfa}K$ has been linked are prepared and added by using flexizyme to conduct translation. Here, the tRNA used in (i) is recognized by an initiation factor and matches with an initiation AUG codon, while the tRNA used in (ii) is recognized by an elongation factor and matches with an AUG codon. It is therefore possible to introduce two amino acids only by removing one amino acid, that is, methionine. In the translated peptide, the chloroacetyl group at the N terminal and the mercapto group of cysteine on the C terminal side have been cyclized therebetween through a thioether bond. A peptide library having trifluoroacetyllysine in the random sequence thereof is synthesized and moreover, the peptide is linked, at the C terminal thereof, to the mRNA via Pu (puromycin).

Acquisition of Inhibitory Peptide

The above-mentioned peptide library is screened by various in vitro display methods such as mRNA display method and ribosome display method and peptides that bind to SIRT2 are selected.

Since a library of peptides containing a special amino acid that binds to a target active site is used, even if screening is conducted with only binding as an indicator, there is a high possibility of the peptide thus obtained binding to the target active site and inhibiting its activity.

Construction of Peptide Library Against Different Target

If, in addition to the deacetylation enzyme such as SIRT2 described above, an inhibitor that binds to an active pocket of various enzymes and thereby inhibits their enzyme activity is known, it is possible to construct a library of peptides having such enzymes introduced therein as a special amino acid as in the case of SIRT2 and acquire an inhibitory peptide. For example, a peptide containing N$^\varepsilon$-propargyllysine is known to serve as an inhibitor of histon demethylation enzyme so that similar to Example, a stronger peptide inhibitor against histon demethylation enzyme can be obtained by screening a library of peptides containing this amino acid [5)].

There is known an example of preparing, as an inhibitor, a peptide having an ATP analogue structure in the side chain thereof by making use of the fact that various ATP analogues serve as an inhibitor of kinase [6)]. Using the technology of the present application makes it possible to create a stronger specific inhibitor by constructing a library of peptides containing a special amino acid having this ATP analogue structure and screening the library for various kinases.

EXAMPLE

The present invention will hereinafter be described specifically. These examples are exemplary only and are not intended to limit the scope of the invention.

Purification of His-SIRT2

Since SIRT2 should be fixed to a substrate upon mRNA display, it was expressed in *Escherichia coli* as a construct having, at the N terminal, a 10×His tag and purified by using the His-tag.

NNK mRNA Library

First, a double-stranded DNA having the following sequence was prepared (in the following, only the forward strand is described in the 5' to 3' direction).

```
                                          (SEQ ID NO: 9)
TAATACGACTCACTATAGGGTTAACTTTAAGAAGGAGATATACAT (ATG) (NNK)₁(NNK)₂ . . . (NNK)ₘ(ATG) (NNK)₁

(NNK)₂ . . . (NNK)ₙ(TGC) (GGC) (AGC) (GGC) (AGC)

(GGC) (AGC) (TAG) GACGGGGGGCGGAAA
```

(In the translation region, one codon is shown in parentheses; N represents any one of A, T, G, and C; K represents either one of T and G; and the combination (m,n) is selected from the following five combinations (m,n)=(3,4), (4,4), (4,5), (5,5), and (5,6))

Then, it was transcribed by using T7 RNA polymerase to obtain an mRNA represented by the following sequence:

```
                                            (SEQ ID NO: 10)
GGGUUAACUUUAAGAAGGAGAUAUACAU(AUG)(NNK)₁

(NNK)₂ . . . (NNK)ₘ(AUG)(NNK)₁(NNK)₂ . . . (NNK)ₙ

(UGC)(GGC)(AGC)(GGC)(AGC)(GGC)(AGC)(UAG)GACGGGGGG

CGGAAA
(N represents any one of A, U, G, and C; and K
represents either one of U and G)
```

NNC mRNA Library

First, a double-stranded DNA having the following sequence was prepared (in the following, only the forward strand is described in the 5' to 3' direction).

```
                                            (SEQ ID NO: 11)
TAATACGACTCACTATAGGGTTAACTTTAAGAAGGAGATATACAT(ATG)

(NNC)₁(NNC)₂ . . . (NNC)ₘ(ATG)(NNC)₁(NNC)₂ . . .

(NNC)ₙ(TGC)(GGC)(AGC)(GGC)(AGC)(GGC)(AGC)(TAG)

GACGGGGGCGGAAA
(In the translation region, one codon is shown in
parentheses; N represents any one of A, T, G,
and C; and the combination of (m, n) is selected
from the following five combinations (m, n) =
(3, 4), (4, 4), (4, 5), (5, 5), and (5, 6))
```

Then, it was transcribed by using T7 RNA polymerase to obtain an mRNA represented by the following sequence:

```
                                            (SEQ ID NO: 12)
GGGUUAACUUUAAGAAGGAGAUAUACAU(AUG)(NNC)₁(NNC)₂ . . .

(NNC)ₘ(AUG)(NNC)₁(NNC)₂ . . . (NNC)ₙ(UGC)(GGC)(AGC)

(GGC)(AGC)(GGC)(AGC)(UAG)GACGGGGGCGGAAA
(N represents any one of A, U, G, and C)
``` mRNA Display

Peptides that bound to SIRT2 were selected from a random peptide library by repeating the following cycle from "linking to puromycin linker" to "amplification of sequence information of collected peptides" (FIG. 1).

Linking to Puromycin Linker

A puromycin linker having the below-described sequence was annealed with the above-mentioned mRNA library and they were linked to each other via T4 RNA Ligase. (SPC18 represents PEG having C and O in the total number of 18).

```
                                            (SEQ ID NO: 13)
        pdCTCCCGCCCCCCGTCC(SPC18)₅CC(Pu)
```

Translation

Figure 2:
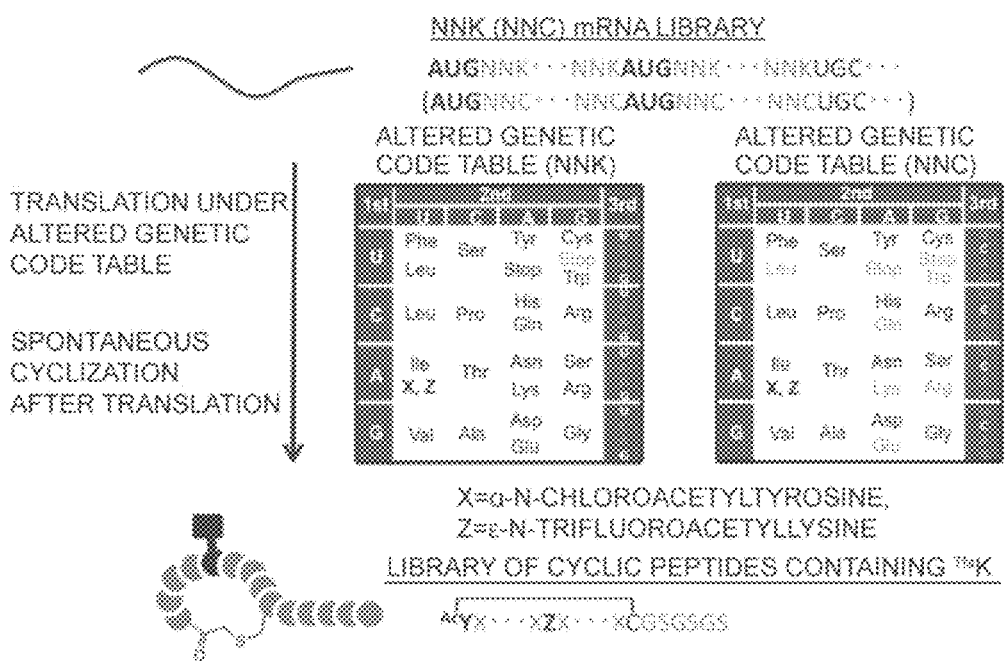
FIG. 2 shows construction of a peptide library through translation by using an altered genetic code table.

The mRNA linked to the linker was translated using an altered genetic code table (FIG. 2). In the present Example, translation was conducted by using a translation system constructed by removing methionine from typical 20 amino acids and adding thereto two tRNAs prepared using flexizyme, that is, (i) tRNA$^{fMet}_{CAU}$ to which α-N-chloroacetyl-L-tyrosine (ClAc-$^L$Y) or α-N-chloroacetyl-D-tyrosine (ClAc-$^D$Y) had been linked and (ii) tRNA$^{AsnE2}_{CAU}$ to which $^{Tfa}$K has been linked. As a result of the translation, a library of peptides which contained, in the random sequence thereof, trifluoroacetyllysine and had been cyclized through a thioether bond was synthesized.

Acquisition of Peptide Binding to SIRT2

The special cyclic peptide library thus prepared was mixed with SIRT2 immobilized on TALON beads, followed by stirring at 4° C. for 30 minutes. The supernatant was removed by using a magnet and the remaining magnetic particles were washed with a buffer. A PCR solution was added to the beads and the resulting mixture was heated at 95° C. for 5 minutes. The peptide was extracted from the beads and the supernatant was collected.

Amplification of Sequence Information of Peptide Thus Collected

The peptide-mRNA binding to SIRT2 thus collected was amplified as a DNA by reverse transcription and PCR. The DNA thus obtained was transcribed into the corresponding mRNA.

Identification of Peptide Sequence Selected

When the recovery of the peptide-mRNA became saturated after repeating the above-mentioned series of operations, TA cloning was conducted with the amplified DNA and the peptide sequence thus obtained was identified.

Evaluation of Inhibitory Activity of Peptides Against SIRT2

In an evaluation system using fluorescence, the inhibitory activity of the selected peptides against SIRT2 was studied. More specifically, first, peptides to be deacetylated with SIRT2 each having, at both ends thereof, a fluorescent group and a quenching group is deacetylated by mixing with SIRT2. When the resulting peptides are reacted with protease that cleaves only a deacetylated peptide, the quenching group is dissociated from the fluorescent group of only the peptides deacetylated with SIRT2 and fluorescence is emitted. During this deacetylation reaction, presence of an inhibitor against SIRT2 retards the progress of deacetylation of the substrate peptide and fluorescence intensity obtained in the end decreases. This means that the inhibitory ability of the selected peptides can be evaluated by the intensity of fluorescence observed in the end.

Results

In order to acquire a peptide that binds to the active pocket of SIRT2 and thereby inhibits its activity, a library of peptides each containing, in the sequence thereof, at least one $^{Tfa}$K (the above-mentioned NNK mRNA library and NNC mRNA library) was constructed, followed by selection using the mRNA display method.

(A) NNK mRNA Library

When the NNK mRNA library is translated, the AUG codon at any position in the random sequence is translated into $^{Tfa}$K and a library of cyclic peptides containing at least one $^{Tfa}$K is formed. When mRNA display was conducted using this peptide library, the recovery of the mRNA became saturated on the fourth round in the peptide library using either of ClAc-$^L$Y or ClAc-$^D$Y. As a result of identification of the peptide sequence after the third round, it has been found that all of the sequences had two or more $^{Tfa}$K (Table 1). 1L-01 to 10 correspond to SEQ ID NOS: 14 to 23, respectively and 1D-01 to 06 correspond to SEQ ID NOS: 24 to 29, respectively.

TABLE 1

Peptide sequence selected from NNK mRNA library
Any sequence has, after the terminal C thereof,
GSGSGS (SEQ ID NO: 70).

| | | | |
|---|---|---|---|
| 1L-01 | XTZKAQZNGZRLSC | 1D-01 | XNGLRPZNHSWRZC |
| 1L-02 | XWFAKZZTYGLQZC | 1D-02 | XZYPCRZTSRVZZC |
| 1L-03 | XNSLZVZSSARIZC | 1D-03 | XDRZTZZEYTZC |
| 1L-04 | XSRZSLZPLZNRC | 1D-04 | XTRZAPZSTZRSC |
| 1L-05 | XGVRRRZSRZZNC | 1D-05 | XZZSNRZLTTZTNC |
| 1L-06 | XSRWZSQZSWC | 1D-06 | XWTZQKQZVHLVZC |
| 1L-07 | XRVTTZZVASPPZC | | |
| 1L-08 | XZRLTFZZTSRAC | | |
| 1L-09 | XKZSRDZHNZRKC | | |
| 1L-10 | XYRZSAZTQSLRZC | | |

In clones with L, X represents α-N-chloroacetyl-L-tyrosine, while in clones with D, it represents α-N-chloroacetyl-D-tyrosine. Z represents ε-N-trifluoroacetyllysine. Translated peptides are cyclized via a thioether bond between the chloroacetyl group at the N terminal and the cysteine residue at the C terminal.

The above results suggest that $^{Tfa}$K is involved in binding of a peptide to SIRT2 and it is presumed that the peptide thus obtained does not only bind to SIRT2 but has inhibitory effect against it. There is however the fear that since no homology is found among sequences other than $^{Tfa}$K, the peptide thus obtained may nonspecifically inhibit the protein of a surtuin family having an active pocket for deacetylation. An NNC mRNA library was therefore prepared, followed by mRNA display.

(B) NNC mRNA Library

When an NNC mRNA library is translated, an AUG codon in the random sequence is translated into $^{Tfa}$K and a library of cyclic peptides containing, in one sequence thereof, only one $^{Tfa}$K is formed. As a result of mRNA display by using this peptide library, the recovery became saturated on the fifth round when ClAc-$^L$Y was used and on the sixth round when ClAc-$^D$Y was used. When identification of the peptide sequence was therefore conducted after the fourth round and the fifth round, respectively, high homology was found in the sequences in the vicinity of $^{Tfa}$K (Table 2). 2L-01 to 21 correspond to SEQ ID NOS: 30 to 50, respectively, and 2D-01 to 19 correspond to SEQ ID NOS: 51 to 69, respectively.

TABLE 2

Peptide sequence selected from NNC mRNA library
Sequences other than 2D-11 and -13
have, after the terminal C thereof,
GSGSGS (SEQ ID NO: 70).

| | | | |
|---|---|---|---|
| 2L-01 | XHHFTIZRFTNSYC | 2D-01 | XYCLNIZRYCNYC |
| 2L-02 | XRNFALZHHINYPC | 2D-02 | XNHSYIZVRSINC |
| 2L-03 | XHNHRVZCYTYSCC | 2D-03 | XYNTIIZTYGC |
| 2L-04 | XVNNRNZRSIRHIC | 2D-04 | XSFTYTZSYSIRC |
| 2L-05 | XHTYHNZRRTNYYC | 2D-05 | XSHSFVZTYSRDC |
| 2L-06 | XYGHRIZSYHYYHC | 2D-06 | XTCNRIZRYNFNHC |
| 2L-07 | XFAYHIZRFSNNPC | 2D-07 | XHSPNVZRYIYIHC |
| 2L-08 | XSNFRIZRYSNSSC | 2D-08 | XHDYRIZRYHTYPC |
| 2L-09 | XYCNXVZRSIHYSC | 2D-09 | XHNYRIZRYATSTC |
| 2L-10 | XTNYTIZTYSNNRC | 2D-10 | XPNYTIZRHSTNYC |
| 2L-11 | XVNHRVZRYYNNHC | 2D-11 | XNHSTIZCYPYZRQRQ . . . |
| 2L-12 | XSSAIIZHYCPCNC | 2D-12 | XHYYRVZRYSSTTC |
| 2L-13 | XTRNHIZRYTFSVC | 2D-13 | XTHYSSZSYNNVZRQRQ . . . |
| 2L-14 | XGNYYTZRYSYYHC | 2D-14 | XCNRICZRTVNTC |
| 2L-15 | XYCNIVZTYGHNHC | 2D-15 | XINRHIZHYTHRYC |
| 2L-16 | XNNFNIZTYSRYTC | 2D-16 | XSHYTIZRYALCC |
| 2L-17 | XYPSHVZHYSSYTC | 2D-17 | XVNHRIZTYTRNC |
| 2L-18 | XNDLRIZRYNAYDC | 2D-18 | XCGSHCZRNIRNC |
| 2L-19 | XNNNRIZRYNFCYC | 2D-19 | XRNYRVZRYNTNHC |
| 2L-20 | XTSSRVZRYSYSFC | | |
| 2L-21 | XVPYYVZSYRRDSC | | |

X and Z have the same meanings as described in TABLE 1. Translated peptide is cyclized via a thioether bond between the chloroacetyl group at the N terminal and the cysteine residue at the C terminal.

Figure 3:
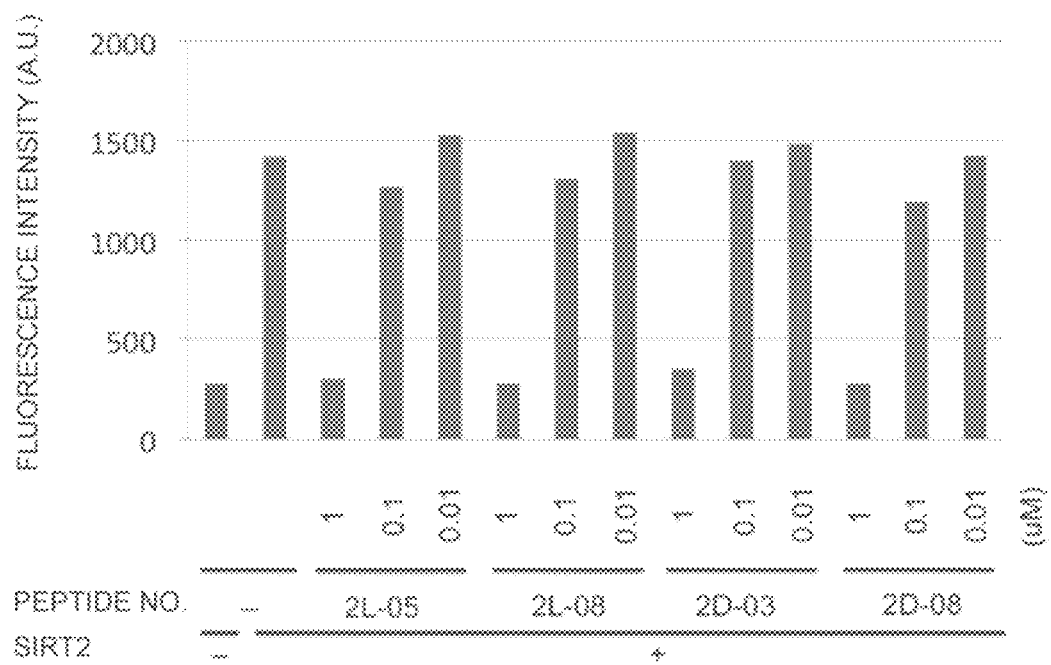
FIG. 3 shows inhibitory activity evaluation of selected peptides. The lower fluorescence intensity shows the stronger inhibitory activity of SIRT2. The leftmost bar shows the background in the absence of SIRT2, while the second left bar indicates the fluorescence intensity in the absence of an inhibitor.

Four peptides (2L-05, 2L-08, 2D-03, and 2D-08) obtained from the NNC mRNA library as described above were synthesized on a solid phase. Evaluation of the inhibitory ability against SIRT2 in a fluorescence-using system has revealed that all the peptides thus synthesized completely suppressed the activity of SIRT2 at 1 μM (FIG. 3).

Moreover, the dissociation constant $K_d$ and inhibition constant $IC_{50}$ of two (2L-08 and 2D-08) of these peptides were determined, showing that they had $K_d$ not greater than 3 nM and $IC_{50}$ not greater than 4 nM and thus, exhibited considerably strong activity.

REFERENCE

1) T. F. Outeiro, et al. Science 317 516-519 (2007).
2) R. Luthi-Carter et al. Proc. Natl. Acad. Sci. USA. 107 7927-32 (2010).
3) J. C. Milne and J. M. Denu Curr. Opin. Chem. Biol. 12 11-17 (2008).
4) a) B. C. Simith, and J. M. Denu J. Am. Chem. Soc. 129 5802-5803 (2009). b) B. C. Simith, and J. M. Denu Biochemistry 46 14478-14486 (2009). c) B. C. Simith, and J. M. Denu J. Biol. Chem. 282 37256-37265.
5) Jeffrey C. Culhane, et al. 128 4536-4537 J. Am. Chem. Soc. (2006)
6) Keykavous Parang, et al. 8 37-41 Nat. struct. Biol. (2001)

Sequence Listing Free Text
SEQ ID NO: 1: flexizyme Fx
SEQ ID NO: 2: dinitrobenzylflexizyme dFx
SEQ ID NO: 3: enhanced flexizyme eFx
SEQ ID NO: 4: aminoflexizyme aFx
SEQ ID NO: 5: tRNA$^{Asn-E2}$
SEQ ID NO: 6: tRNA$^{fMet}$
SEQ ID NO: 7: tRNA$^{Asn}$ of *Escherichia coli*

SEQ ID NO: 8: tRNA^fMet of *Escherichia coli*
SEQ ID NO: 9: General sequence of template DNA of NKK mRNA library
SEQ ID NO: 10: General sequence of NKK mRNA library
SEQ ID NO: 11: General sequence of template DNA of NKC mRNA library
SEQ ID NO: 12: General sequence of NKC mRNA library
SEQ ID NO: 13: Base sequence of DNA portion of puromycin linker
SEQ ID NOS: 14 to 29: Amino acid sequences of members of NNK mRNA library
SEQ ID NOS: 30 to 69: Amino acid sequences of members of NNC mRNA library

```
                       SEQUENCE LISTING

<160> NUMBER OF SEQ IDS NOS: 77

<210> SEQ ID NO 1
  <211> LENGTH: 45
  <212> TYPE: RNA
  <213> ORGANISM: Artificial Sequence
  <220> FEATURE:
  <223> OTHER INFORMATION: Nucleic acid sequence of Flexizyme Fx.

<400> SEQUENCE: 1
ggaucgaaag auuuccgcag gcccgaaagg guauuggcgu uaggu              45

<210> SEQ ID NO 2
  <211> LENGTH: 46
  <212> TYPE: RNA
  <213> ORGANISM: Artificial Sequence
  <220> FEATURE:
  <223> OTHER INFORMATION: Nucleic acid sequence of dinitrobenzyl-
        Flexizyme dFx.

<400> SEQUENCE: 2
ggaucgaaag auuuccgcau ccccgaaagg guacauggcg uuaggu             46

<210> SEQ ID NO 3
  <211> LENGTH: 45
  <212> TYPE: RNA
  <213> ORGANISM: Artificial Sequence
  <220> FEATURE:
  <223> OTHER INFORMATION: Nucleic acid sequence of enhanced Flexizyme
        eFx.

<400> SEQUENCE: 3
ggaucgaaag auuuccgcgg ccccgaaagg ggauuagcgu uaggu              45

<210> SEQ ID NO 4
  <211> LENGTH: 47
  <212> TYPE: RNA
  <213> ORGANISM: Artificial Sequence
  <220> FEATURE:
  <223> OTHER INFORMATION: Nucleic acid sequence of amino-Flexizyme aFx.

<400> SEQUENCE: 4
ggaucgaaag auuuccgcac ccccgaaagg gguaaguggc guuaggu            47

<210> SEQ ID NO 5
  <211> LENGTH: 76
  <212> TYPE: RNA
  <213> ORGANISM: Artificial Sequence
  <220> FEATURE:
  <223> OTHER INFORMATION: Nucleic acid sequence of tRNA Asn-E2
  <220> FEATURE:
  <221> NAME/KEY: misc_feature
  <222> LOCATION: (34)..(36)
  <223> OTHER INFORMATION: n is any base
  <220> FEATURE:
  <221> NAME/KEY: tRNA
  <222> LOCATION: (34)..(36)

<400> SEQUENCE: 5
ggcucuguag uucagucggu agaacggcgg acunnnaauc cguaugucac ugguucgagu   60
```
ccagucagag ccgcca                                                      76

<210> SEQ ID NO 6
<211> LENGTH: 77
<212> TYPE: RNA
<213> ORGANISM: Artificial Sequence
<220> FEATURE:
<223> OTHER INFORMATION: Nucleic acid sequence of tRNA fMet

<400> SEQUENCE: 6 ggcgggugg agcagccugg uagcucgucg ggcucauaac ccgaagaucg ucgguucaaa        60
uccggccccc gcaacca                                                     77

<210> SEQ ID NO 7
<211> LENGTH: 76
<212> TYPE: RNA
<213> ORGANISM: Escherichia coli
<220> FEATURE:
<221> NAME/KEY: misc_feature
<223> OTHER INFORMATION: Nucleic acid sequence of tRNA Asn
<220> FEATURE:
<221> NAME/KEY: modified_base
<222> LOCATION: (8)..(8)
<223> OTHER INFORMATION: s4u
<220> FEATURE:
<221> NAME/KEY: misc_feature
<222> LOCATION: (34)..(34)
<223> OTHER INFORMATION: n is queuosine
<220> FEATURE:
<221> NAME/KEY: modified_base
<222> LOCATION: (37)..(37)
<223> OTHER INFORMATION: t6a
<220> FEATURE:
<221> NAME/KEY: modified_base
<222> LOCATION: (46)..(46)
<223> OTHER INFORMATION: m7g
<220> FEATURE:
<221> NAME/KEY: misc_feature
<222> LOCATION: (54)..(54)
<223> OTHER INFORMATION: n is ribothymidine

<400> SEQUENCE: 7
uccucuguag uucagdcggd agaacggcgg acunuuaayc cguaugucac uggnycgagu        60
ccagucagag gagcca                                                      76

<210> SEQ ID NO 8
<211> LENGTH: 77
<212> TYPE: RNA
<213> ORGANISM: Escherichia coli
<220> FEATURE:
<221> NAME/KEY: misc_feature
<223> OTHER INFORMATION: Nucleic acid sequence of tRNA fMet
<220> FEATURE:
<221> NAME/KEY: modified_base
<222> LOCATION: (8)..(8)
<223> OTHER INFORMATION: s4u
<220> FEATURE:
<221> NAME/KEY: modified_base
<222> LOCATION: (33)..(33)
<223> OTHER INFORMATION: 2'-O-methylcytidine
<220> FEATURE:
<221> NAME/KEY: misc_feature
<222> LOCATION: (55)..(55)
<223> OTHER INFORMATION: n is ribothymidine

<400> SEQUENCE: 8 cgcgggugg agcagccugg dagcucgucg ggcucauaac ccgaagaucg ucggnycaaa        60
uccggccccc gcaacca                                                     77

```
<210> SEQ ID NO 9
<211> LENGTH: 123
<212> TYPE: DNA
<213> ORGANISM: Artificial Sequence
<220> FEATURE:
<223> OTHER INFORMATION: Nucleic acid sequence of DNA template for NNK
      mRNA Library.
<220> FEATURE:
<221> NAME/KEY: misc_feature
<222> LOCATION: (49)..(50)
<223> OTHER INFORMATION: Each n stands for a, t, g or c.
<220> FEATURE:
<221> NAME/KEY: misc_feature
<222> LOCATION: (49)..(84)
<223> OTHER INFORMATION: If # of n's on 5' side of atg is 9 then # of
      n's on 3' side of atg is 12; If # of n's on 5' side of atg is 12
      then # of n's on 3' side of atg is 12 or 15; If # of n's on 5'
      side of atg is 15 then # of n's on 3' side of atg is 15 or 18.
<220> FEATURE:
<221> NAME/KEY: misc_feature
<222> LOCATION: (51)..(51)
<223> OTHER INFORMATION: n stands for t or g.
<220> FEATURE:
<221> NAME/KEY: misc_feature
<222> LOCATION: (52)..(53)
<223> OTHER INFORMATION: Each n stands for a, t, g or c.
<220> FEATURE:
<221> NAME/KEY: misc_feature
<222> LOCATION: (54)..(54)
<223> OTHER INFORMATION: n stands for t or g.
<220> FEATURE:
<221> NAME/KEY: misc_feature
<222> LOCATION: (55)..(56)
<223> OTHER INFORMATION: Each n stands for a, t, g or c.
<220> FEATURE:
<221> NAME/KEY: misc_feature
<222> LOCATION: (57)..(57)
<223> OTHER INFORMATION: n stands for t or g.
<220> FEATURE:
<221> NAME/KEY: misc_feature
<222> LOCATION: (58)..(59)
<223> OTHER INFORMATION: Each n stands for a, t, g or c.
<220> FEATURE:
<221> NAME/KEY: misc_feature
<222> LOCATION: (60)..(60)
<223> OTHER INFORMATION: n stands for t or g.
<220> FEATURE:
<221> NAME/KEY: misc_feature
<222> LOCATION: (61)..(62)
<223> OTHER INFORMATION: Each n stands for a, t, g or c.
<220> FEATURE:
<221> NAME/KEY: misc_feature
<222> LOCATION: (63)..(63)
<223> OTHER INFORMATION: n stands for t or g.
<220> FEATURE:
<221> NAME/KEY: misc_feature
<222> LOCATION: (67)..(68)
<223> OTHER INFORMATION: Each n stands for a, t, g or c.
<220> FEATURE:
<221> NAME/KEY: misc_feature
<222> LOCATION: (69)..(69)
<223> OTHER INFORMATION: n stands for t or g.
<220> FEATURE:
<221> NAME/KEY: misc_feature
<222> LOCATION: (70)..(71)
<223> OTHER INFORMATION: Each n stands for a, t, g or c.
<220> FEATURE:
<221> NAME/KEY: misc_feature
<222> LOCATION: (72)..(72)
<223> OTHER INFORMATION: n stands for t or g.
<220> FEATURE:
<221> NAME/KEY: misc_feature
<222> LOCATION: (73)..(74)
<223> OTHER INFORMATION: Each n stands for a, t, g or c.
<220> FEATURE:
<221> NAME/KEY: misc_feature
<222> LOCATION: (75)..(75)
<223> OTHER INFORMATION: n stands for t or g.
```

-continued

```
<220> FEATURE:
<221> NAME/KEY: misc_feature
<222> LOCATION: (76)..(77)
<223> OTHER INFORMATION: Each n stands for a, t, g or c.
<220> FEATURE:
<221> NAME/KEY: misc_feature
<222> LOCATION: (78)..(78)
<223> OTHER INFORMATION: n stands for t or g.
<220> FEATURE:
<221> NAME/KEY: misc_feature
<222> LOCATION: (79)..(80)
<223> OTHER INFORMATION: Each n stands for a, t, g or c.
<220> FEATURE:
<221> NAME/KEY: misc_feature
<222> LOCATION: (81)..(81)
<223> OTHER INFORMATION: n stands for t or g.
<220> FEATURE:
<221> NAME/KEY: misc_feature
<222> LOCATION: (82)..(83)
<223> OTHER INFORMATION: Each n stands for a, t, g or c.
<220> FEATURE:
<221> NAME/KEY: misc_feature
<222> LOCATION: (84)..(84)
<223> OTHER INFORMATION: n stands for t or g.

<400> SEQUENCE: 9
taatacgact cactataggg ttaactttaa gaaggagata tacatatgnn nnnnnnnnn      60 nnnatgnnnn nnnnnnnnnn nnnntgcggc agcggcagcg gcagctagga cggggggcgg    120
aaa                                                                 123

<210> SEQ ID NO 10
<211> LENGTH: 106
<212> TYPE: RNA
<213> ORGANISM: Artificial Sequence
<220> FEATURE:
<223> OTHER INFORMATION: Nucleic acid sequence of members of NNK mRNA
      Library.
<220> FEATURE:
<221> NAME/KEY: misc_feature
<222> LOCATION: (32)..(33)
<223> OTHER INFORMATION: Each n stands for a, u, g or c.
<220> FEATURE:
<221> NAME/KEY: misc_feature
<222> LOCATION: (32)..(67)
<223> OTHER INFORMATION: If # of n's on 5' side of atg is 9 # of n's on
      3' side of atg is 12; If # of n's on 5' side of atg is 12 # of
      n's on 3' side of atg is 12 or 15; If # of n's on 5' side of atg
      is 15 # of n's on 3' side of atg is 15 or 18.
<220> FEATURE:
<221> NAME/KEY: misc_feature
<222> LOCATION: (34)..(34)
<223> OTHER INFORMATION: n stands for u or g.
<220> FEATURE:
<221> NAME/KEY: misc_feature
<222> LOCATION: (35)..(36)
<223> OTHER INFORMATION: Each n stands for a, u, g or c.
<220> FEATURE:
<221> NAME/KEY: misc_feature
<222> LOCATION: (37)..(37)
<223> OTHER INFORMATION: n stands for u or g.
<220> FEATURE:
<221> NAME/KEY: misc_feature
<222> LOCATION: (38)..(39)
<223> OTHER INFORMATION: Each n stands for a, u, g or c.
<220> FEATURE:
<221> NAME/KEY: misc_feature
<222> LOCATION: (40)..(40)
<223> OTHER INFORMATION: n stands for u or g.
<220> FEATURE:
<221> NAME/KEY: misc_feature
<222> LOCATION: (41)..(42)
<223> OTHER INFORMATION: Each n stands for a, u, g or c.
<220> FEATURE:
<221> NAME/KEY: misc_feature
<222> LOCATION: (43)..(43)
```

```
<223> OTHER INFORMATION: n stands for u or g.
<220> FEATURE:
<221> NAME/KEY: misc_feature
<222> LOCATION: (44)..(45)
<223> OTHER INFORMATION: Each n stands for a, u, g or c.
<220> FEATURE:
<221> NAME/KEY: misc_feature
<222> LOCATION: (46)..(46)
<223> OTHER INFORMATION: n stands for u or g.
<220> FEATURE:
<221> NAME/KEY: misc_feature
<222> LOCATION: (50)..(51)
<223> OTHER INFORMATION: Each n stands for a, u, g or c.
<220> FEATURE:
<221> NAME/KEY: misc_feature
<222> LOCATION: (52)..(52)
<223> OTHER INFORMATION: n stands for u or g.
<220> FEATURE:
<221> NAME/KEY: misc_feature
<222> LOCATION: (53)..(54)
<223> OTHER INFORMATION: Each n stands for a, u, g or c.
<220> FEATURE:
<221> NAME/KEY: misc_feature
<222> LOCATION: (55)..(55)
<223> OTHER INFORMATION: n stands for u or g.
<220> FEATURE:
<221> NAME/KEY: misc_feature
<222> LOCATION: (56)..(57)
<223> OTHER INFORMATION: Each n stands for a, u, g or c.
<220> FEATURE:
<221> NAME/KEY: misc_feature
<222> LOCATION: (58)..(58)
<223> OTHER INFORMATION: n stands for u or g.
<220> FEATURE:
<221> NAME/KEY: misc_feature
<222> LOCATION: (59)..(60)
<223> OTHER INFORMATION: Each n stands for a, u, g or c.
<220> FEATURE:
<221> NAME/KEY: misc_feature
<222> LOCATION: (61)..(61)
<223> OTHER INFORMATION: n stands for u or g.
<220> FEATURE:
<221> NAME/KEY: misc_feature
<222> LOCATION: (62)..(63)
<223> OTHER INFORMATION: Each n stands for a, u, g or c.
<220> FEATURE:
<221> NAME/KEY: misc_feature
<222> LOCATION: (64)..(64)
<223> OTHER INFORMATION: n stands for u or g.
<220> FEATURE:
<221> NAME/KEY: misc_feature
<222> LOCATION: (65)..(66)
<223> OTHER INFORMATION: Each n stands for a, u, g or c.
<220> FEATURE:
<221> NAME/KEY: misc_feature
<222> LOCATION: (67)..(67)
<223> OTHER INFORMATION: n stands for u or g.

<400> SEQUENCE: 10
ggguuaacuu uaagaaggag auauacauau gnnnnnnnnn nnnnnnaugn nnnnnnnnnn      60
nnnnnnnugc ggcagcggca gcggcagcua ggacgggggg cggaaa                   106

<210> SEQ ID NO 11
<211> LENGTH: 123
<212> TYPE: DNA
<213> ORGANISM: Artificial Sequence
<220> FEATURE:
<223> OTHER INFORMATION: Nucleic acid sequence of DNA template for NNC
      mRNA Library.
<220> FEATURE:
<221> NAME/KEY: misc_feature
<222> LOCATION: (49)..(50)
<223> OTHER INFORMATION: Each n stands for a, t, g or c.
<220> FEATURE:
<221> NAME/KEY: misc_feature
<222> LOCATION: (49)..(84)
```

```
<223> OTHER INFORMATION: If nnc's on 5' side of atg repeated 3X nnc's
      on 3' side of atg are repeated 4X; If nnc's on 5' side of atg
      repeated 4X nnc's on 3' side of atg are repeated 4X or 5X; If
      nnc's on 5' side of atg repeated 5X nnc's on 3' side of atg are
      repeated 5X or 6X.
<220> FEATURE:
<221> NAME/KEY: misc_feature
<222> LOCATION: (52)..(53)
<223> OTHER INFORMATION: Each n stands for a, t, g or c.
<220> FEATURE:
<221> NAME/KEY: misc_feature
<222> LOCATION: (55)..(56)
<223> OTHER INFORMATION: Each n stands for a, t, g or c.
<220> FEATURE:
<221> NAME/KEY: misc_feature
<222> LOCATION: (58)..(59)
<223> OTHER INFORMATION: Each n stands for a, t, g or c.
<220> FEATURE:
<221> NAME/KEY: misc_feature
<222> LOCATION: (61)..(62)
<223> OTHER INFORMATION: Each n stands for a, t, g or c.
<220> FEATURE:
<221> NAME/KEY: misc_feature
<222> LOCATION: (67)..(68)
<223> OTHER INFORMATION: Each n stands for a, t, g or c.
<220> FEATURE:
<221> NAME/KEY: misc_feature
<222> LOCATION: (70)..(71)
<223> OTHER INFORMATION: Each n stands for a, t, g or c.
<220> FEATURE:
<221> NAME/KEY: misc_feature
<222> LOCATION: (73)..(74)
<223> OTHER INFORMATION: Each n stands for a, t, g or c.
<220> FEATURE:
<221> NAME/KEY: misc_feature
<222> LOCATION: (76)..(77)
<223> OTHER INFORMATION: Each n stands for a, t, g or c.
<220> FEATURE:
<221> NAME/KEY: misc_feature
<222> LOCATION: (79)..(80)
<223> OTHER INFORMATION: Each n stands for a, t, g or c.
<220> FEATURE:
<221> NAME/KEY: misc_feature
<222> LOCATION: (82)..(83)
<223> OTHER INFORMATION: Each n stands for a, t, g or c.

<400> SEQUENCE: 11
taatacgact cactataggg ttaactttaa gaaggagata tacatatgnn cnncnncnnc      60
nncatgnncn ncnncnncnn cnnctgcggc agcggcagcg gcagctagga cgggggggcgg   120 aaa                                                                  123

<210> SEQ ID NO 12
<211> LENGTH: 106
<212> TYPE: RNA
<213> ORGANISM: Artificial Sequence
<220> FEATURE:
<223> OTHER INFORMATION: Nucleic acid sequence of members of NNC mRNA
      Library.
<220> FEATURE:
<221> NAME/KEY: misc_feature
<222> LOCATION: (32)..(33)
<223> OTHER INFORMATION: Each n stands for a, u, g or c.
<220> FEATURE:
<221> NAME/KEY: misc_feature
<222> LOCATION: (32)..(67)
<223> OTHER INFORMATION: If nnc's on 5' side of atg repeated 3X nnc's on
      3' side of atg are repeated 4X; If nnc's on 5' side of atg
      repeated 4X nnc's on 3' side of atg are repeated 4X or 5X; If
      nnc's on 5' side of atg repeated 5X nnc's on 3' side of atg are
      repeated 5X or 6X.
<220> FEATURE:
<221> NAME/KEY: misc_feature
<222> LOCATION: (35)..(36)
<223> OTHER INFORMATION: Each n stands for a, u, g or c.
<220> FEATURE:
```

```
<221> NAME/KEY: misc_feature
<222> LOCATION: (38)..(39)
<223> OTHER INFORMATION: Each n stands for a, u, g or c.
<220> FEATURE:
<221> NAME/KEY: misc_feature
<222> LOCATION: (41)..(42)
<223> OTHER INFORMATION: Each n stands for a, u, g or c.
<220> FEATURE:
<221> NAME/KEY: misc_feature
<222> LOCATION: (44)..(45)
<223> OTHER INFORMATION: Each n stands for a, u, g or c.
<220> FEATURE:
<221> NAME/KEY: misc_feature
<222> LOCATION: (50)..(51)
<223> OTHER INFORMATION: Each n stands for a, u, g or c.
<220> FEATURE:
<221> NAME/KEY: misc_feature
<222> LOCATION: (53)..(54)
<223> OTHER INFORMATION: Each n stands for a, u, g or c.
<220> FEATURE:
<221> NAME/KEY: misc_feature
<222> LOCATION: (56)..(57)
<223> OTHER INFORMATION: Each n stands for a, u, g or c.
<220> FEATURE:
<221> NAME/KEY: misc_feature
<222> LOCATION: (59)..(60)
<223> OTHER INFORMATION: Each n stands for a, u, g or c.
<220> FEATURE:
<221> NAME/KEY: misc_feature
<222> LOCATION: (62)..(63)
<223> OTHER INFORMATION: Each n stands for a, u, g or c.
<220> FEATURE:
<221> NAME/KEY: misc_feature
<222> LOCATION: (65)..(66)
<223> OTHER INFORMATION: Each n stands for a, u, g or c.

<400> SEQUENCE: 12
ggguuaacuu uaagaaggag auauacauau gnncnncnnc nncnncaugn ncnncnncnn      60
cnncnncugc ggcagcggca gcggcagcua ggacgggggg cggaaa                   106

<210> SEQ ID NO 13
<211> LENGTH: 16
<212> TYPE: DNA
<213> ORGANISM: Artificial Sequence
<220> FEATURE:
<223> OTHER INFORMATION: Nucleic acid sequence of DNA contained in
      puromycin linker.
<220> FEATURE:
<221> NAME/KEY: misc_feature
<223> OTHER INFORMATION: 5'-OH of the DNA is monophosphorylated

<400> SEQUENCE: 13
ctcccgcccc ccgtcc                                                     16

<210> SEQ ID NO 14
<211> LENGTH: 20
<212> TYPE: PRT
<213> ORGANISM: Artificial Sequence
<220> FEATURE:
<223> OTHER INFORMATION: Amino acid sequence of 1L-01 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (3)..(3)
<223> OTHER INFORMATION: Xaa stands for epsilon-N-trifluoroacetyl lysine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine
<220> FEATURE:
<221> NAME/KEY: MISC_FEATURE
```

```
<222> LOCATION: (10)..(10)
<223> OTHER INFORMATION: Xaa stands for epsilon-N-trifluoroacetyl lysine

<400> SEQUENCE: 14

Xaa Thr Xaa Lys Ala Gln Xaa Asn Gly Xaa Arg Leu Ser Cys Gly Ser
1               5                   10                  15

Gly Ser Gly Ser
            20

<210> SEQ ID NO 15
<211> LENGTH: 20
<212> TYPE: PRT
<213> ORGANISM: Artificial Sequence
<220> FEATURE:
<223> OTHER INFORMATION: Amino acid sequence of 1L-02 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (6)..(6)
<223> OTHER INFORMATION: Xaa stands for epsilon-N-trifluoroacetyl lysine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine
<220> FEATURE:
<221> NAME/KEY: MISC_FEATURE
<222> LOCATION: (13)..(13)
<223> OTHER INFORMATION: Xaa stands for epsilon-N-trifluoroacetyl lysine

<400> SEQUENCE: 15

Xaa Trp Phe Ala Lys Xaa Xaa Thr Tyr Gly Leu Gln Xaa Cys Gly Ser
1               5                   10                  15

Gly Ser Gly Ser
            20

<210> SEQ ID NO 16
<211> LENGTH: 20
<212> TYPE: PRT
<213> ORGANISM: Artificial Sequence
<220> FEATURE:
<223> OTHER INFORMATION: Amino acid sequence of 1L-03 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (5)..(5)
<223> OTHER INFORMATION: Xaa stands for epsilon-N-trifluoroacetyl lysine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine
<220> FEATURE:
<221> NAME/KEY: MISC_FEATURE
<222> LOCATION: (13)..(13)
<223> OTHER INFORMATION: Xaa stands for epsilon-N-trifluoroacetyl lysine

<400> SEQUENCE: 16

Xaa Asn Ser Leu Xaa Val Xaa Ser Ser Ala Arg Ile Xaa Cys Gly Ser
1               5                   10                  15

Gly Ser Gly Ser
            20

<210> SEQ ID NO 17
<211> LENGTH: 19
<212> TYPE: PRT
```

```
<213> ORGANISM: Artificial Sequence
<220> FEATURE:
<223> OTHER INFORMATION: Amino acid sequence of 1L-04 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (4)..(4)
<223> OTHER INFORMATION: Xaa stands for epsilon-N-trifluoroacetyl lysine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine
<220> FEATURE:
<221> NAME/KEY: MISC_FEATURE
<222> LOCATION: (10)..(10)
<223> OTHER INFORMATION: Xaa stands for epsilon-N-trifluoroacetyl lysine

<400> SEQUENCE: 17

Xaa Ser Arg Xaa Ser Leu Xaa Pro Leu Xaa Asn Arg Cys Gly Ser Gly
1               5                   10                  15

Ser Gly Ser

<210> SEQ ID NO 18
<211> LENGTH: 19
<212> TYPE: PRT
<213> ORGANISM: Artificial Sequence
<220> FEATURE:
<223> OTHER INFORMATION: Amino acid sequence of 1L-05 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine
<220> FEATURE:
<221> NAME/KEY: MISC_FEATURE
<222> LOCATION: (10)..(10)
<223> OTHER INFORMATION: Xaa stands for epsilon-N-trifluoroacetyl lysine
<220> FEATURE:
<221> NAME/KEY: MISC_FEATURE
<222> LOCATION: (11)..(11)
<223> OTHER INFORMATION: Xaa stands for epsilon-N-trifluoroacetyl lysine

<400> SEQUENCE: 18

Xaa Gly Val Arg Arg Arg Xaa Ser Arg Xaa Xaa Asn Cys Gly Ser Gly
1               5                   10                  15

Ser Gly Ser

<210> SEQ ID NO 19
<211> LENGTH: 17
<212> TYPE: PRT
<213> ORGANISM: Artificial Sequence
<220> FEATURE:
<223> OTHER INFORMATION: Amino acid sequence of 1L-06 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (5)..(5)
<223> OTHER INFORMATION: Xaa stands for epsilon-N-trifluoroacetyl lysine
<220> FEATURE:
<221> NAME/KEY: MISC_FEATURE
<222> LOCATION: (8)..(8)
<223> OTHER INFORMATION: Xaa stands for epsilon-N-trifluoroacetyl lysine

<400> SEQUENCE: 19
```

```
Xaa Ser Arg Trp Xaa Ser Gln Xaa Ser Trp Cys Gly Ser Gly Ser Gly
1               5                   10                  15

Ser

<210> SEQ ID NO 20
<211> LENGTH: 20
<212> TYPE: PRT
<213> ORGANISM: Artificial Sequence
<220> FEATURE:
<223> OTHER INFORMATION: Amino acid sequence 1L-07 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (6)..(6)
<223> OTHER INFORMATION: Xaa stands for epsilon-N-trifluoroacetyl lysine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine
<220> FEATURE:
<221> NAME/KEY: MISC_FEATURE
<222> LOCATION: (13)..(13)
<223> OTHER INFORMATION: Xaa stands for epsilon-N-trifluoroacetyl lysine

<400> SEQUENCE: 20

Xaa Arg Val Thr Thr Xaa Xaa Val Ala Ser Pro Pro Xaa Cys Gly Ser
1               5                   10                  15

Gly Ser Gly Ser
            20

<210> SEQ ID NO 21
<211> LENGTH: 19
<212> TYPE: PRT
<213> ORGANISM: Artificial Sequence
<220> FEATURE:
<223> OTHER INFORMATION: Amino acid sequence of 1L-08 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (2)..(2)
<223> OTHER INFORMATION: Xaa stands for epsilon-N-trifluoroacetyl lysine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine
<220> FEATURE:
<221> NAME/KEY: MISC_FEATURE
<222> LOCATION: (8)..(8)
<223> OTHER INFORMATION: Xaa stands for epsilon-N-trifluoroacetyl lysine

<400> SEQUENCE: 21

Xaa Xaa Arg Leu Thr Phe Xaa Xaa Thr Ser Arg Ala Cys Gly Ser Gly
1               5                   10                  15

Ser Gly Ser

<210> SEQ ID NO 22
<211> LENGTH: 19
<212> TYPE: PRT
<213> ORGANISM: Artificial Sequence
<220> FEATURE:
<223> OTHER INFORMATION: Amino acid sequence of 1L-09 peptide.
<220> FEATURE:
<221> NAME/KEY: MISC_FEATURE
<222> LOCATION: (1)..(1)
```

```
<223> OTHER INFORMATION: Xaa stands for alpha-N-chloroacetyl-L-tyrosine
<220> FEATURE:
<221> NAME/KEY: MISC_FEATURE
<222> LOCATION: (3)..(3)
<223> OTHER INFORMATION: Xaa stands for epsilon-N-trifluoroacetyl lysine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine
<220> FEATURE:
<221> NAME/KEY: MISC_FEATURE
<222> LOCATION: (10)..(10)
<223> OTHER INFORMATION: Xaa stands for epsilon-N-trifluoroacetyl lysine

<400> SEQUENCE: 22

Xaa Lys Xaa Ser Arg Asp Xaa His Asn Xaa Arg Lys Cys Gly Ser Gly
1               5                   10                  15

Ser Gly Ser

<210> SEQ ID NO 23
<211> LENGTH: 20
<212> TYPE: PRT
<213> ORGANISM: Artificial Sequence
<220> FEATURE:
<223> OTHER INFORMATION: Amino acid sequence of 1L-10 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (4)..(4)
<223> OTHER INFORMATION: Xaa stands for epsilon-N-trifluoroacetyl lysine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine
<220> FEATURE:
<221> NAME/KEY: MISC_FEATURE
<222> LOCATION: (13)..(13)
<223> OTHER INFORMATION: Xaa stands for epsilon-N-trifluoroacetyl lysine

<400> SEQUENCE: 23

Xaa Tyr Arg Xaa Ser Ala Xaa Thr Gln Ser Leu Arg Xaa Cys Gly Ser
1               5                   10                  15

Gly Ser Gly Ser
            20

<210> SEQ ID NO 24
<211> LENGTH: 20
<212> TYPE: PRT
<213> ORGANISM: Artificial Sequence
<220> FEATURE:
<223> OTHER INFORMATION: Amino acid sequence of 1D-01 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine
<220> FEATURE:
<221> NAME/KEY: MISC_FEATURE
<222> LOCATION: (13)..(13)
<223> OTHER INFORMATION: Xaa stands for epsilon-N-trifluoroacetyl lysine

<400> SEQUENCE: 24

Xaa Asn Gly Leu Arg Pro Xaa Asn His Ser Trp Arg Xaa Cys Gly Ser
1               5                   10                  15

Gly Ser Gly Ser
```

-continued

```
<210> SEQ ID NO 25
<211> LENGTH: 20
<212> TYPE: PRT
<213> ORGANISM: Artificial Sequence
<220> FEATURE:
<223> OTHER INFORMATION: Amino acid sequence of 1D-02 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (2)..(2)
<223> OTHER INFORMATION: Xaa stands for epsilon-N-trifluoroacetyl lysine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine
<220> FEATURE:
<221> NAME/KEY: MISC_FEATURE
<222> LOCATION: (12)..(12)
<223> OTHER INFORMATION: Xaa stands for epsilon-N-trifluoroacetyl lysine
<220> FEATURE:
<221> NAME/KEY: MISC_FEATURE
<222> LOCATION: (13)..(13)
<223> OTHER INFORMATION: Xaa stands for epsilon-N-trifluoroacetyl lysine

<400> SEQUENCE: 25

Xaa Xaa Tyr Pro Cys Arg Xaa Thr Ser Arg Val Xaa Xaa Cys Gly Ser
1               5                   10                  15

Gly Ser Gly Ser
            20

<210> SEQ ID NO 26
<211> LENGTH: 18
<212> TYPE: PRT
<213> ORGANISM: Artificial Sequence
<220> FEATURE:
<223> OTHER INFORMATION: Amino acid sequence of 1D-03 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (4)..(4)
<223> OTHER INFORMATION: Xaa stands for epsilon-N-trifluoroacetyl lysine
<220> FEATURE:
<221> NAME/KEY: MISC_FEATURE
<222> LOCATION: (6)..(6)
<223> OTHER INFORMATION: Xaa stands for epsilon-N-trifluoroacetyl lysine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine
<220> FEATURE:
<221> NAME/KEY: MISC_FEATURE
<222> LOCATION: (11)..(11)
<223> OTHER INFORMATION: Xaa stands for epsilon-N-trifluoroacetyl lysine

<400> SEQUENCE: 26

Xaa Asp Arg Xaa Thr Xaa Xaa Glu Tyr Thr Xaa Cys Gly Ser Gly Ser
1               5                   10                  15

Gly Ser

<210> SEQ ID NO 27
<211> LENGTH: 19
<212> TYPE: PRT
<213> ORGANISM: Artificial Sequence
<220> FEATURE:
```

```
<223> OTHER INFORMATION: Amino acid sequence of 1D-04 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (4)..(4)
<223> OTHER INFORMATION: Xaa stands for epsilon-N-trifluoroacetyl lysine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine
<220> FEATURE:
<221> NAME/KEY: MISC_FEATURE
<222> LOCATION: (10)..(10)
<223> OTHER INFORMATION: Xaa stands for epsilon-N-trifluoroacetyl lysine

<400> SEQUENCE: 27

Xaa Thr Arg Xaa Ala Pro Xaa Ser Thr Xaa Arg Ser Cys Gly Ser Gly
1               5                   10                  15

Ser Gly Ser

<210> SEQ ID NO 28
<211> LENGTH: 20
<212> TYPE: PRT
<213> ORGANISM: Artificial Sequence
<220> FEATURE:
<223> OTHER INFORMATION: Amino acid sequence of 1D-05 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (2)..(2)
<223> OTHER INFORMATION: Xaa stands for epsilon-N-trifluoroacetyl lysine
<220> FEATURE:
<221> NAME/KEY: MISC_FEATURE
<222> LOCATION: (3)..(3)
<223> OTHER INFORMATION: Xaa stands for epsilon-N-trifluoroacetyl lysine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine
<220> FEATURE:
<221> NAME/KEY: MISC_FEATURE
<222> LOCATION: (11)..(11)
<223> OTHER INFORMATION: Xaa stands for epsilon-N-trifluoroacetyl lysine

<400> SEQUENCE: 28

Xaa Xaa Xaa Ser Asn Arg Xaa Leu Thr Thr Xaa Thr Asn Cys Gly Ser
1               5                   10                  15

Gly Ser Gly Ser
            20

<210> SEQ ID NO 29
<211> LENGTH: 20
<212> TYPE: PRT
<213> ORGANISM: Artificial Sequence
<220> FEATURE:
<223> OTHER INFORMATION: Amino acid sequence of 1D-06 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (4)..(4)
<223> OTHER INFORMATION: Xaa stands for epsilon-N-trifluoroacetyl lysine
<220> FEATURE:
<221> NAME/KEY: MISC_FEATURE
<222> LOCATION: (7)..(7)
```

<223> OTHER INFORMATION: Xaa stands for epsilon-N-trifluoroacetyl lysine
<220> FEATURE:
<221> NAME/KEY: MISC_FEATURE
<222> LOCATION: (13)..(13)
<223> OTHER INFORMATION: Xaa stands for epsilon-N-trifluoroacetyl lysine

<400> SEQUENCE: 29

Xaa Trp Thr Xaa Gln Lys Xaa Gln Val His Leu Val Xaa Cys Gly Ser
1               5                   10                  15

Gly Ser Gly Ser
            20

<210> SEQ ID NO 30
<211> LENGTH: 20
<212> TYPE: PRT
<213> ORGANISM: Artificial Sequence
<220> FEATURE:
<223> OTHER INFORMATION: Amino acid sequence of 2L-01 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 30

Xaa His His Phe Thr Ile Xaa Arg Phe Thr Asn Ser Tyr Cys Gly Ser
1               5                   10                  15

Gly Ser Gly Ser
            20

<210> SEQ ID NO 31
<211> LENGTH: 20
<212> TYPE: PRT
<213> ORGANISM: Artificial Sequence
<220> FEATURE:
<223> OTHER INFORMATION: Amino acid sequence of 2L-02 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 31

Xaa Arg Asn Phe Ala Leu Xaa His His Ile Asn Tyr Pro Cys Gly Ser
1               5                   10                  15

Gly Ser Gly Ser
            20

<210> SEQ ID NO 32
<211> LENGTH: 20
<212> TYPE: PRT
<213> ORGANISM: Artificial Sequence
<220> FEATURE:
<223> OTHER INFORMATION: Amino acid sequence of 2L-03 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 32

Xaa His Asn His Arg Val Xaa Cys Tyr Thr Tyr Ser Cys Cys Gly Ser
1               5                   10                  15

Gly Ser Gly Ser
            20

<210> SEQ ID NO 33
<211> LENGTH: 20
<212> TYPE: PRT
<213> ORGANISM: Artificial Sequence
<220> FEATURE:
<223> OTHER INFORMATION: Amino acid sequence of 2L-04 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 33

Xaa Val Asn Asn Arg Val Xaa Arg Ser Ile Arg His Ile Cys Gly Ser
1               5                   10                  15

Gly Ser Gly Ser
            20

<210> SEQ ID NO 34
<211> LENGTH: 20
<212> TYPE: PRT
<213> ORGANISM: Artificial Sequence
<220> FEATURE:
<223> OTHER INFORMATION: Amino acid sequence of 2L-05 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 34

Xaa His Thr Tyr His Val Xaa Arg Arg Thr Asn Tyr Tyr Cys Gly Ser
1               5                   10                  15

Gly Ser Gly Ser
            20

<210> SEQ ID NO 35
<211> LENGTH: 20
<212> TYPE: PRT
<213> ORGANISM: Artificial Sequence
<220> FEATURE:
<223> OTHER INFORMATION: Amino acid sequence of 2L-06 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 35

Xaa Tyr Gly His Arg Ile Xaa Ser Tyr His Tyr Tyr His Cys Gly Ser
1               5                   10                  15

Gly Ser Gly Ser
            20

<210> SEQ ID NO 36
<211> LENGTH: 20
<212> TYPE: PRT
<213> ORGANISM: Artificial Sequence
<220> FEATURE:
<223> OTHER INFORMATION: Amino acid sequence of 2L-07 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 36

Xaa Phe Ala Tyr His Ile Xaa Arg Phe Ser Asn Asn Pro Cys Gly Ser
1               5                   10                  15

Gly Ser Gly Ser
            20

<210> SEQ ID NO 37
<211> LENGTH: 20
<212> TYPE: PRT
<213> ORGANISM: Artificial Sequence
<220> FEATURE:
<223> OTHER INFORMATION: Amino acid sequence of 2L-08 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 37

Xaa Ser Asn Phe Arg Ile Xaa Arg Tyr Ser Asn Ser Ser Cys Gly Ser
1               5                   10                  15

Gly Ser Gly Ser
            20

<210> SEQ ID NO 38
<211> LENGTH: 20
<212> TYPE: PRT
<213> ORGANISM: Artificial Sequence
<220> FEATURE:
<223> OTHER INFORMATION: Amino acid sequence of 2L-09 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 38

Xaa Tyr Cys Asn Cys Val Xaa Arg Ser Ile His Tyr Ser Cys Gly Ser
1               5                   10                  15

Gly Ser Gly Ser
            20

<210> SEQ ID NO 39
<211> LENGTH: 20
<212> TYPE: PRT
<213> ORGANISM: Artificial Sequence
<220> FEATURE:
<223> OTHER INFORMATION: Amino acid sequence of 2L-10 peptide.

```
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 39

Xaa Thr Asn Tyr Thr Ile Xaa Thr Tyr Ser Asn Asn Arg Cys Gly Ser
1               5                   10                  15

Gly Ser Gly Ser
            20

<210> SEQ ID NO 40
<211> LENGTH: 20
<212> TYPE: PRT
<213> ORGANISM: Artificial Sequence
<220> FEATURE:
<223> OTHER INFORMATION: Amino acid sequence of 2L-11 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 40

Xaa Val Asn His Arg Val Xaa Arg Tyr Tyr Asn Asn His Cys Gly Ser
1               5                   10                  15

Gly Ser Gly Ser
            20

<210> SEQ ID NO 41
<211> LENGTH: 20
<212> TYPE: PRT
<213> ORGANISM: Artificial Sequence
<220> FEATURE:
<223> OTHER INFORMATION: Amino acid sequence of 2L-12 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 41

Xaa Ser Ser Ala Ile Ile Xaa His Tyr Cys Pro Cys Asn Cys Gly Ser
1               5                   10                  15

Gly Ser Gly Ser
            20

<210> SEQ ID NO 42
<211> LENGTH: 20
<212> TYPE: PRT
<213> ORGANISM: Artificial Sequence
<220> FEATURE:
<223> OTHER INFORMATION: Amino acid sequence of 2L-13 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (7)..(7)
```

```
<223> OTHER INFORMATION: Xaa stands for epsilon-N-trifluoroacetyl lysine

<400> SEQUENCE: 42

Xaa Thr Arg Asn His Ile Xaa Arg Tyr Thr Phe Ser Val Cys Gly Ser
1               5                   10                  15

Gly Ser Gly Ser
            20

<210> SEQ ID NO 43
<211> LENGTH: 20
<212> TYPE: PRT
<213> ORGANISM: Artificial Sequence
<220> FEATURE:
<223> OTHER INFORMATION: Amino acid sequence of 2L-14 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 43

Xaa Gly Asn Tyr Tyr Ile Xaa Arg Tyr Ser Tyr Tyr His Cys Gly Ser
1               5                   10                  15

Gly Ser Gly Ser
            20

<210> SEQ ID NO 44
<211> LENGTH: 20
<212> TYPE: PRT
<213> ORGANISM: Artificial Sequence
<220> FEATURE:
<223> OTHER INFORMATION: Amino acid sequence of 2L-15 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 44

Xaa Tyr Cys Asn Ile Val Xaa Thr Tyr Gly His Asn His Cys Gly Ser
1               5                   10                  15

Gly Ser Gly Ser
            20

<210> SEQ ID NO 45
<211> LENGTH: 20
<212> TYPE: PRT
<213> ORGANISM: Artificial Sequence
<220> FEATURE:
<223> OTHER INFORMATION: Amino acid sequence of 2L-16 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 45

Xaa Asn Asn Phe His Ile Xaa Thr Tyr Ser Arg Tyr Thr Cys Gly Ser
1               5                   10                  15
```

Gly Ser Gly Ser
        20

<210> SEQ ID NO 46
<211> LENGTH: 20
<212> TYPE: PRT
<213> ORGANISM: Artificial Sequence
<220> FEATURE:
<223> OTHER INFORMATION: Amino acid sequence of 2L-17 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 46

Xaa Tyr Pro Ser His Val Xaa His Tyr Ser Ser Tyr Thr Cys Gly Ser
1               5                   10                  15

Gly Ser Gly Ser
        20

<210> SEQ ID NO 47
<211> LENGTH: 20
<212> TYPE: PRT
<213> ORGANISM: Artificial Sequence
<220> FEATURE:
<223> OTHER INFORMATION: Amino acid sequence of 2L-18 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 47

Xaa Asn Asp Leu Arg Ile Xaa Arg Tyr Asn Ala Tyr Asp Cys Gly Ser
1               5                   10                  15

Gly Ser Gly Ser
        20

<210> SEQ ID NO 48
<211> LENGTH: 20
<212> TYPE: PRT
<213> ORGANISM: Artificial Sequence
<220> FEATURE:
<223> OTHER INFORMATION: Amino acid sequence of 2L-19 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 48

Xaa Asn Asn Asn Arg Ile Xaa Arg Tyr Asn Phe Cys Tyr Cys Gly Ser
1               5                   10                  15

Gly Ser Gly Ser
        20

<210> SEQ ID NO 49
<211> LENGTH: 20
<212> TYPE: PRT

```
<213> ORGANISM: Artificial Sequence
<220> FEATURE:
<223> OTHER INFORMATION: Amino acid sequence of 2L-20 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 49

Xaa Thr Ser Ser Arg Val Xaa Arg Tyr Ser Tyr Ser Phe Cys Gly Ser
1               5                   10                  15

Gly Ser Gly Ser
            20

<210> SEQ ID NO 50
<211> LENGTH: 20
<212> TYPE: PRT
<213> ORGANISM: Artificial Sequence
<220> FEATURE:
<223> OTHER INFORMATION: Amino acid sequence of 2L-21 peptide.
<220> FEATURE:
<221> NAME/KEY: MISC_FEATURE
<222> LOCATION: (1)..(1)
<223> OTHER INFORMATION: Xaa stands for alpha-N-chloroacetyl-L-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 50

Xaa Val Pro Tyr Tyr Val Xaa Ser Tyr Arg Arg Asp Ser Cys Gly Ser
1               5                   10                  15

Gly Ser Gly Ser
            20

<210> SEQ ID NO 51
<211> LENGTH: 19
<212> TYPE: PRT
<213> ORGANISM: Artificial Sequence
<220> FEATURE:
<223> OTHER INFORMATION: Amino acid sequence of 2D-01 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 51

Xaa Tyr Cys Leu Asn Ile Xaa Arg Tyr Cys Asn Tyr Cys Gly Ser Gly
1               5                   10                  15

Ser Gly Ser

<210> SEQ ID NO 52
<211> LENGTH: 19
<212> TYPE: PRT
<213> ORGANISM: Artificial Sequence
<220> FEATURE:
<223> OTHER INFORMATION: Amino acid sequence of 2D-02 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
```

```
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 52

Xaa Asn His Ser Tyr Ile Xaa Val Arg Ser Ile Asn Cys Gly Ser Gly
1               5                   10                  15

Ser Gly Ser

<210> SEQ ID NO 53
<211> LENGTH: 17
<212> TYPE: PRT
<213> ORGANISM: Artificial Sequence
<220> FEATURE:
<223> OTHER INFORMATION: Amino acid sequence of 2D-03 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 53

Xaa Tyr Asn Thr Ile Ile Xaa Thr Tyr Gly Cys Gly Ser Gly Ser Gly
1               5                   10                  15

Ser

<210> SEQ ID NO 54
<211> LENGTH: 19
<212> TYPE: PRT
<213> ORGANISM: Artificial Sequence
<220> FEATURE:
<223> OTHER INFORMATION: Amino acid sequence of 2D-04 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 54

Xaa Ser Phe Thr Tyr Thr Xaa Ser Tyr Ser Ile Arg Cys Gly Ser Gly
1               5                   10                  15

Ser Gly Ser

<210> SEQ ID NO 55
<211> LENGTH: 19
<212> TYPE: PRT
<213> ORGANISM: Artificial Sequence
<220> FEATURE:
<223> OTHER INFORMATION: Amino acid sequence of 2D-05 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 55

Xaa Ser His Ser Phe Val Xaa Thr Tyr Ser Arg Asp Cys Gly Ser Gly
1               5                   10                  15

Ser Gly Ser
```

```
<210> SEQ ID NO 56
<211> LENGTH: 20
<212> TYPE: PRT
<213> ORGANISM: Artificial Sequence
<220> FEATURE:
<223> OTHER INFORMATION: Amino acid sequence of 2D-06 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 56

Xaa Thr Cys Asn Arg Ile Xaa Arg Tyr Asn Phe Asn His Cys Gly Ser
1               5                   10                  15

Gly Ser Gly Ser
            20

<210> SEQ ID NO 57
<211> LENGTH: 20
<212> TYPE: PRT
<213> ORGANISM: Artificial Sequence
<220> FEATURE:
<223> OTHER INFORMATION: Amino acid sequence of 2D-07 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 57

Xaa His Ser Pro Asn Val Xaa Arg Tyr Ile Tyr Ile His Cys Gly Ser
1               5                   10                  15

Gly Ser Gly Ser
            20

<210> SEQ ID NO 58
<211> LENGTH: 20
<212> TYPE: PRT
<213> ORGANISM: Artificial Sequence
<220> FEATURE:
<223> OTHER INFORMATION: Amino acid sequence of 2D-08 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 58

Xaa His Asp Tyr Arg Ile Xaa Arg Tyr His Thr Tyr Pro Cys Gly Ser
1               5                   10                  15

Gly Ser Gly Ser
            20

<210> SEQ ID NO 59
<211> LENGTH: 20
<212> TYPE: PRT
<213> ORGANISM: Artificial Sequence
<220> FEATURE:
```

```
<223> OTHER INFORMATION: Amino acid sequence of 2D-09 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 59

Xaa His Asn Tyr Arg Ile Xaa Arg Tyr Ala Thr Ser Thr Cys Gly Ser
1               5                   10                  15

Gly Ser Gly Ser
            20

<210> SEQ ID NO 60
<211> LENGTH: 20
<212> TYPE: PRT
<213> ORGANISM: Artificial Sequence
<220> FEATURE:
<223> OTHER INFORMATION: Amino acid sequence of 2D-10 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 60

Xaa Pro Asn Tyr Thr Ile Glx Arg His Ser Thr Asn Tyr Cys Gly Ser
1               5                   10                  15

Gly Ser Gly Ser
            20

<210> SEQ ID NO 61
<211> LENGTH: 16
<212> TYPE: PRT
<213> ORGANISM: Artificial Sequence
<220> FEATURE:
<223> OTHER INFORMATION: Amino acid sequence of 2D-11 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine
<220> FEATURE:
<221> NAME/KEY: MISC_FEATURE
<222> LOCATION: (12)..(12)
<223> OTHER INFORMATION: Xaa stands for epsilon-N-trifluoroacetyl lysine

<400> SEQUENCE: 61

Xaa Asn His Ser Thr Ile Xaa Cys Tyr Pro Tyr Xaa Arg Gln Arg Gln
1               5                   10                  15

<210> SEQ ID NO 62
<211> LENGTH: 20
<212> TYPE: PRT
<213> ORGANISM: Artificial Sequence
<220> FEATURE:
<223> OTHER INFORMATION: Amino acid sequence of 2D-12 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
```

-continued

```
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 62

Xaa His Tyr Tyr Arg Val Xaa Arg Tyr Ser Ser Thr Thr Cys Gly Ser
1               5                   10                  15

Gly Ser Gly Ser
            20

<210> SEQ ID NO 63
<211> LENGTH: 17
<212> TYPE: PRT
<213> ORGANISM: Artificial Sequence
<220> FEATURE:
<223> OTHER INFORMATION: Amino acid sequence of 2D-13 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine
<220> FEATURE:
<221> NAME/KEY: MISC_FEATURE
<222> LOCATION: (13)..(13)
<223> OTHER INFORMATION: Xaa stands for epsilon-N-trifluoroacetyl lysine

<400> SEQUENCE: 63

Xaa Thr His Tyr Ser Ser Xaa Ser Tyr Asn Asn Val Xaa Arg Gln Arg
1               5                   10                  15

Gln

<210> SEQ ID NO 64
<211> LENGTH: 19
<212> TYPE: PRT
<213> ORGANISM: Artificial Sequence
<220> FEATURE:
<223> OTHER INFORMATION: Amino acid sequence of 2D-14 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 64

Xaa Cys Asn Arg Ile Cys Xaa Arg Thr Val Asn Thr Cys Gly Ser Gly
1               5                   10                  15

Ser Gly Ser

<210> SEQ ID NO 65
<211> LENGTH: 20
<212> TYPE: PRT
<213> ORGANISM: Artificial Sequence
<220> FEATURE:
<223> OTHER INFORMATION: Amino acid sequence of 2D-15 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 65
```

```
Xaa Ile Asn Arg His Ile Xaa His Tyr Thr His Arg Tyr Cys Gly Ser
1               5                   10                  15

Gly Ser Gly Ser
            20

<210> SEQ ID NO 66
<211> LENGTH: 19
<212> TYPE: PRT
<213> ORGANISM: Artificial Sequence
<220> FEATURE:
<223> OTHER INFORMATION: Amino acid sequence of 2D-16 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 66

Xaa Ser His Tyr Thr Ile Xaa Arg Tyr Ala Leu Cys Cys Gly Ser Gly
1               5                   10                  15

Ser Gly Ser

<210> SEQ ID NO 67
<211> LENGTH: 19
<212> TYPE: PRT
<213> ORGANISM: Artificial Sequence
<220> FEATURE:
<223> OTHER INFORMATION: Amino acid sequence of 2D-17 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 67

Xaa Val Asn His Arg Ile Xaa Thr Tyr Thr Arg Asn Cys Gly Ser Gly
1               5                   10                  15

Ser Gly Ser

<210> SEQ ID NO 68
<211> LENGTH: 19
<212> TYPE: PRT
<213> ORGANISM: Artificial Sequence
<220> FEATURE:
<223> OTHER INFORMATION: Amino acid sequence of 2D-18 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 68

Xaa Cys Gly Ser His Cys Xaa Arg Asn Ile Arg Asn Cys Gly Ser Gly
1               5                   10                  15

Ser Gly Ser

<210> SEQ ID NO 69
<211> LENGTH: 20
```

```
<212> TYPE: PRT
<213> ORGANISM: Artificial Sequence
<220> FEATURE:
<223> OTHER INFORMATION: Amino acid sequence of 2D-19 peptide.
<220> FEATURE:
<221> NAME/KEY: MISC_FEATURE
<222> LOCATION: (1)..(1)
<223> OTHER INFORMATION: Xaa stands for alpha-N-chloroacetyl-D-tyrosine
<220> FEATURE:
<221> NAME/KEY: MISC_FEATURE
<222> LOCATION: (7)..(7)
<223> OTHER INFORMATION: Xaa stands for epsilon-N-trifluoroacetyl lysine

<400> SEQUENCE: 69

Xaa Arg Asn Tyr Arg Val Glx Arg Tyr Asn Thr Asn His Cys Gly Ser
1               5                   10                  15

Gly Ser Gly Ser
        20

<210> SEQ ID NO 70
<211> LENGTH: 6
<212> TYPE: PRT
<213> ORGANISM: Artificial Sequence
<220> FEATURE:
<223> OTHER INFORMATION: Sequence after the terminal C of given peptides.

<400> SEQUENCE: 70

Gly Ser Gly Ser Gly Ser
1               5

<210> SEQ ID NO 71
<211> LENGTH: 6
<212> TYPE: RNA
<213> ORGANISM: Artificial Sequence
<220> FEATURE:
<223> OTHER INFORMATION: First part of nucleic acid sequence of members
      of NNK mRNA library shown in Figure 2.
<220> FEATURE:
<221> NAME/KEY: MISC_FEATURE
<222> LOCATION: (4)..(4)
<223> OTHER INFORMATION: N stands for A, U, G or C
<220> FEATURE:
<221> NAME/KEY: MISC_FEATURE
<222> LOCATION: (5)..(5)
<223> OTHER INFORMATION: N stands for A, U, G or C
<220> FEATURE:
<221> NAME/KEY: MISC_FEATURE
<222> LOCATION: (6)..(6)
<223> OTHER INFORMATION: K stands for U or G

<400> SEQUENCE: 71 augnnk                                                           6

<210> SEQ ID NO 72
<211> LENGTH: 9
<212> TYPE: RNA
<213> ORGANISM: Artificial Sequence
<220> FEATURE:
<223> OTHER INFORMATION: Second part of nucleic acid sequence of members
      of NNK mRNA library shown in Figure 2.
<220> FEATURE:
<221> NAME/KEY: MISC_FEATURE
<222> LOCATION: (1)..(1)
<223> OTHER INFORMATION: N stands for A, U, G or C
<220> FEATURE:
<221> NAME/KEY: MISC_FEATURE
<222> LOCATION: (2)..(2)
<223> OTHER INFORMATION: N stands for A, U, G or C
<220> FEATURE:
<221> NAME/KEY: MISC_FEATURE
<222> LOCATION: (3)..(3)
<223> OTHER INFORMATION: K stands for U or G
```

```
<220> FEATURE:
<221> NAME/KEY: MISC_FEATURE
<222> LOCATION: (7)..(7)
<223> OTHER INFORMATION: N stands for A, U, G or C
<220> FEATURE:
<221> NAME/KEY: MISC_FEATURE
<222> LOCATION: (8)..(8)
<223> OTHER INFORMATION: N stands for A, U, G or C
<220> FEATURE:
<221> NAME/KEY: MISC_FEATURE
<222> LOCATION: (9)..(9)
<223> OTHER INFORMATION: K stands for U or G

<400> SEQUENCE: 72 nnkaugnnk                                                                 9

<210> SEQ ID NO 73
<211> LENGTH: 6
<212> TYPE: RNA
<213> ORGANISM: Artificial Sequence
<220> FEATURE:
<223> OTHER INFORMATION: Third part of nucleic acid sequence of members
      of NNK mRNA library shown in Figure 2.
<220> FEATURE:
<221> NAME/KEY: MISC_FEATURE
<222> LOCATION: (1)..(1)
<223> OTHER INFORMATION: N stands for A, U, G or C
<220> FEATURE:
<221> NAME/KEY: MISC_FEATURE
<222> LOCATION: (2)..(2)
<223> OTHER INFORMATION: N stands for A, U, G or C
<220> FEATURE:
<221> NAME/KEY: MISC_FEATURE
<222> LOCATION: (3)..(3)
<223> OTHER INFORMATION: K stands for U or G

<400> SEQUENCE: 73 nnkugc                                                                    6

<210> SEQ ID NO 74
<211> LENGTH: 6
<212> TYPE: RNA
<213> ORGANISM: Artificial Sequence
<220> FEATURE:
<223> OTHER INFORMATION: First part of nucleic acid sequence of members
      of NNC mRNA library shown in Figure 2.
<220> FEATURE:
<221> NAME/KEY: MISC_FEATURE
<222> LOCATION: (4)..(4)
<223> OTHER INFORMATION: N stands for A, U, G or C
<220> FEATURE:
<221> NAME/KEY: MISC_FEATURE
<222> LOCATION: (5)..(5)
<223> OTHER INFORMATION: N stands for A, U, G or C

<400> SEQUENCE: 74 augnnc                                                                    6

<210> SEQ ID NO 75
<211> LENGTH: 9
<212> TYPE: RNA
<213> ORGANISM: Artificial Sequence
<220> FEATURE:
<223> OTHER INFORMATION: Second part of nucleic acid sequence of members
      of NNC mRNA library shown in Figure 2.
<220> FEATURE:
<221> NAME/KEY: MISC_FEATURE
<222> LOCATION: (1)..(1)
<223> OTHER INFORMATION: N stands for A, U, G or C
<220> FEATURE:
<221> NAME/KEY: MISC_FEATURE
<222> LOCATION: (2)..(2)
<223> OTHER INFORMATION: N stands for A, U, G or C
```

```
<220> FEATURE:
<221> NAME/KEY: MISC_FEATURE
<222> LOCATION: (7)..(7)
<223> OTHER INFORMATION: N stands for A, U, G or C
<220> FEATURE:
<221> NAME/KEY: MISC_FEATURE
<222> LOCATION: (8)..(8)
<223> OTHER INFORMATION: N stands for A, U, G or C

<400> SEQUENCE: 75 nncaugnnc                                                         9

<210> SEQ ID NO 76
<211> LENGTH: 6
<212> TYPE: RNA
<213> ORGANISM: Artificial Sequence
<220> FEATURE:
<223> OTHER INFORMATION: Third part of nucleic acid sequence of members
      of NNC mRNA library shown in Figure 2.
<220> FEATURE:
<221> NAME/KEY: MISC_FEATURE
<222> LOCATION: (1)..(1)
<223> OTHER INFORMATION: N stands for A, U, G or C
<220> FEATURE:
<221> NAME/KEY: MISC_FEATURE
<222> LOCATION: (2)..(2)
<223> OTHER INFORMATION: N stands for A, U, G or C

<400> SEQUENCE: 76 nncugc                                                            6

<210> SEQ ID NO 77
<211> LENGTH: 7
<212> TYPE: PRT
<213> ORGANISM: Artificial Sequence
<220> FEATURE:
<223> OTHER INFORMATION: Sequence at the C terminus of the schematically
      shown cyclized peptide in Figure 2.

<400> SEQUENCE: 77

Cys Gly Ser Gly Ser Gly Ser
1               5
```

The invention claimed is:

1. A method for producing a peptide library, comprising:
   (i) selecting a target substance;
   (ii) identifying a low molecular group that is determined to be likely capable of binding to the selected target substance;
   (iii) choosing a special amino acid that is a non-proteinogenic amino acid and contains the identified low molecular group,
   (iv) preparing a library of mRNAs containing, in an mRNA sequence thereof, coding for a random amino acid sequence, a base sequence having an altered codon encoding the special amino acid,
   (v) preparing an aminoacyl tRNA in which the special amino acid has been linked to a tRNA encoded by the altered codon, and
   (vi) translating the mRNAs by using a cell-free translation system containing the aminoacyl tRNA to obtain a library composed of a plurality of peptides, each peptide containing the special amino acid as part of its random amino acid sequence.

2. The method according to claim 1, wherein in the step (v), the aminoacyl tRNA is prepared by transferring, to a tRNA, the special amino acid in the presence of an RNA catalyst having acyl tRNA synthetase-like activity.

3. The method according to claim 1, wherein the altered codon encoding the special amino acid is an AUG codon and the mRNA random sequence is composed of repetition of an NNC or NNU (N represents any one base of A, U, G, and C) triplet.

4. The method according to claim 3, wherein the mRNA random sequence further contains NNK (K represents U or G).

5. The method according to claim 1, further comprising cyclizing each of the peptides.

6. The method according to claim 5, wherein:
   in the step (iv), second and third altered codons coding for two amino acids having functional groups 1 and 2, respectively, as any pair selected from (A) to (C) of Table 1, are placed in the mRNA random sequence, with the proviso that when the amino acid having the functional group 2 is a proteinogenic amino acid, the third altered codon may be replaced by a codon encoding the proteinogenic amino acid,
   in the step (v), an aminoacyl tRNA obtained by linking the amino acid having the functional group 1 to a tRNA encoded by the second altered codon and an aminoacyl tRNA obtained by linking the amino acid having the functional group 2 to a tRNA encoded by the third altered codon are prepared and the step (vi) is conducted using these tRNAs in addition, and after the step (vi), the method includes cyclization through a reaction between the functional groups, and wherein Table 1 is as follows:

TABLE 1

| | Functional group 1 | Functional group 2 |
|---|---|---|
| (A) | 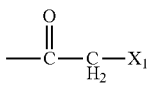<br>(A-1) | HS—<br>(A-2) |
| (B) | —C≡C—H<br>(B-1) | N₃—<br>(B-2) |
| (C) | —Ar—CH₂NH₂<br>(C-1) | 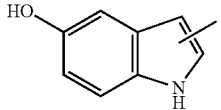<br>(C-2) |

(wherein, $X_1$ represents Cl, Br, or I and Ar represents an aromatic ring which may have a substituent).

wherein $X_1$ represents Cl, Br, or I and Ar represents an aromatic ring which may have a substituent.

7. The method according to claim 1, wherein the step (iv) further comprising binding puromycin, directly or via a linker, to the 3'-end of each mRNAs of the mRNA library thus obtained.

8. A screening method of a peptide library obtained using the method as claimed in claim 1 or a peptide library comprising a peptide produced using the method as claimed in claim 1 to select a peptide capable of binding to a given enzyme, comprising:
bringing the peptide library into contact with the given enzyme, and
selecting a peptide that binds to the given enzyme.

9. A screening method of a peptide library obtained using the method as claimed in claim 1 wherein (a) the step (iv) further comprises binding puromycin, directly or via a linker, to the 3' end of each mRNAs of the mRNA library thus obtained or (b) each of the peptides is linked to an mRNA coding for the peptide to select a peptide capable of binding to a given enzyme, comprising:
bringing the library into contact with the given enzyme,
selecting peptides that binds to the given enzyme and to which an mRNA has been linked,
synthesizing a DNA from the mRNA linked to the selected peptides through reverse transcription,
amplifying the DNA by using PCR, obtaining an mRNA library through transcription, and binding puromycin to the mRNA,
translating the mRNA by using a cell-free translation system to obtain a library of peptides to each of which the mRNA has been linked, and
repeating, at least once, the steps from the step of bringing the library into contact with the given enzyme until the step of obtaining a peptide library.

10. The method according to claim 9, wherein the portion capable of binding to the active site of the given enzyme is a portion of a ligand that binds the active site of the given enzyme.

11. The method according to claim 10, wherein the ligand is a substrate for the given enzyme.

12. The method according to claim 10, wherein the ligand is an inhibitor of the given enzyme.

13. The method according to claim 9, wherein the portion capable of binding to the active site of the given enzyme is predicted to capable of binding to the active site based on structure.

14. The method according to claim 1, wherein the low molecular group has a molecular weight of 100 Da to 1000 Da.

15. The method according to claim 1, wherein the target substance is an enzyme.

* * * * *